United States Patent
Matsumoto et al.

(10) Patent No.: US 8,717,563 B2
(45) Date of Patent: May 6, 2014

(54) LIGHT SCATTERING TYPE PARTICLE DETECTOR USING SCATTERED LIGHT OF SURFACE PLASMON RESONANCE PHOTONS

(75) Inventors: Takahiro Matsumoto, Yokohama (JP); Fumio Kubo, Yokohama (JP); Koichi Okamoto, Fukuoka (JP); Yasuyuki Kawakami, Abiko (JP)

(73) Assignee: Stanley Electric Co., Ltd., Tokyo (JP)

( * ) Notice: Subject to any disclaimer, the term of this patent is extended or adjusted under 35 U.S.C. 154(b) by 250 days.

(21) Appl. No.: 13/313,233

(22) Filed: Dec. 7, 2011

(65) Prior Publication Data
US 2012/0140222 A1 Jun. 7, 2012

(30) Foreign Application Priority Data

Dec. 7, 2010 (JP) .................................. 2010-272404
Nov. 16, 2011 (JP) .................................. 2011-250329

(51) Int. Cl.
  *G01N 21/00* (2006.01)
(52) U.S. Cl.
  USPC ....................................................... 356/338
(58) Field of Classification Search
  USPC ....................................................... 356/338
  See application file for complete search history.

(56) References Cited

U.S. PATENT DOCUMENTS

| 2004/0011974 A1 | 1/2004 | Matsuda et al. |
| 2008/0174774 A1* | 7/2008 | Bratkovski .................. 356/301 |
| 2010/0091274 A1* | 4/2010 | Bratkovski et al. ........... 356/301 |

FOREIGN PATENT DOCUMENTS

| JP | 2002-151765 A | 5/2002 |
| JP | 2002-223019 A | 8/2002 |

OTHER PUBLICATIONS

Takashi Minakami; "Fine Particle Meter Using LD-Excited Solid-State Laser as Light Source"; Oct. 2001; (three sheets).
H. Raether; "Surface Plasmons on Smooth and Rough Surfaces and on Gratings"; vol. 111; Springer-Vertag Berlin Heidelberg, Jun. 24, 1985.

* cited by examiner

*Primary Examiner* — Roy M Punnoose
(74) *Attorney, Agent, or Firm* — Holtz, Holtz, Goodman & Chick, PC

(57) ABSTRACT

A particle detector includes a light source, and a metal layer having an incident/reflective surface and a photoelectric surface opposing the incident/reflective surface. Incident light from the light source reaches the incident/reflective surface to excite near-field surface plasmon resonance photons at the photoelectric surface. A particle deposited on the photoelectric surface of the metal layer changes the near-field surface plasmon resonance photons to far-field scattered light. The particle detector further includes a scattered light detecting unit, provided above the photoelectric surface of the metal layer, for detecting the far-field scattered light.

18 Claims, 26 Drawing Sheets

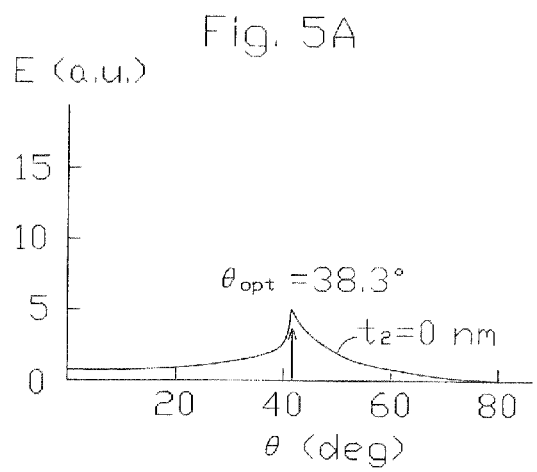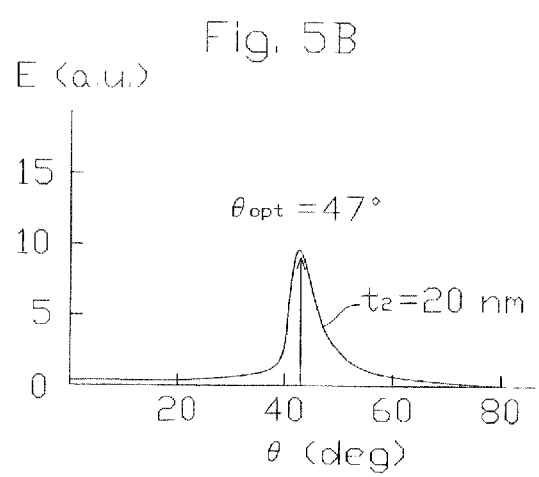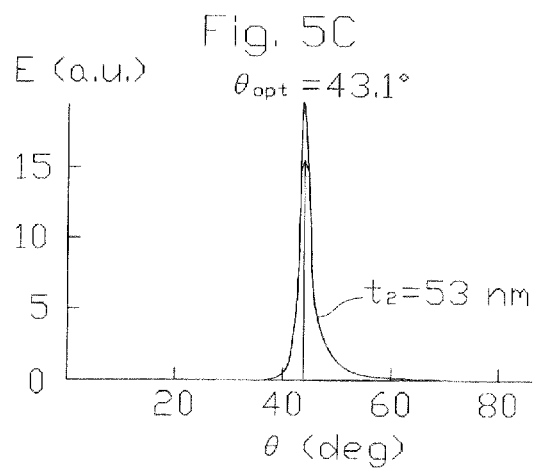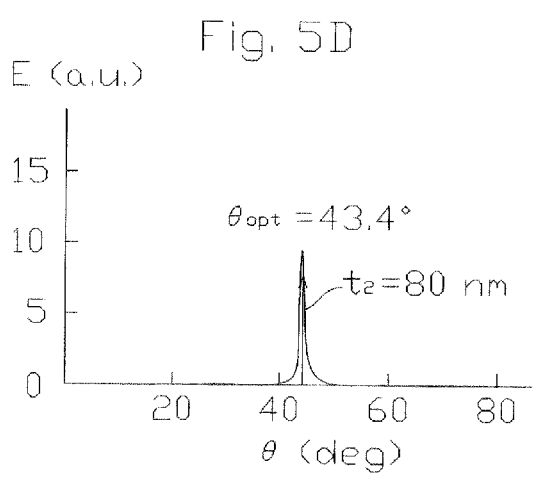

FOR BK-7 PRISM 1
  $n_1 = 1.535$
  $k_1 = 0$

FOR Au LAYER 2
  $t_2 = 53$ nm
  $n_2 = 0.18$
  $k_2 = 3$

FOR $SiO_2$ PROTECTION LAYER 3
  $n_3 = 1.5$
  $k_3 = 0$

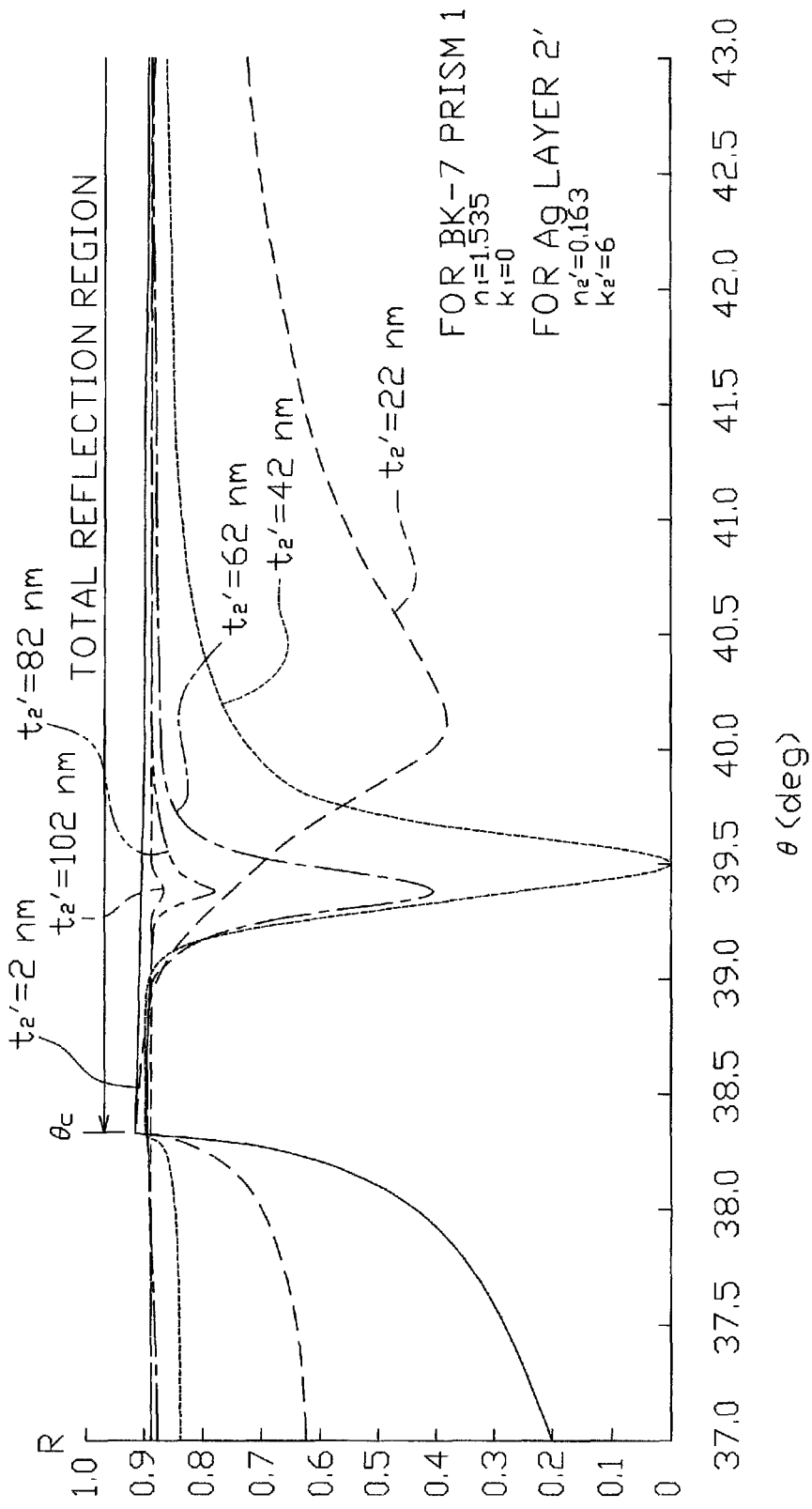

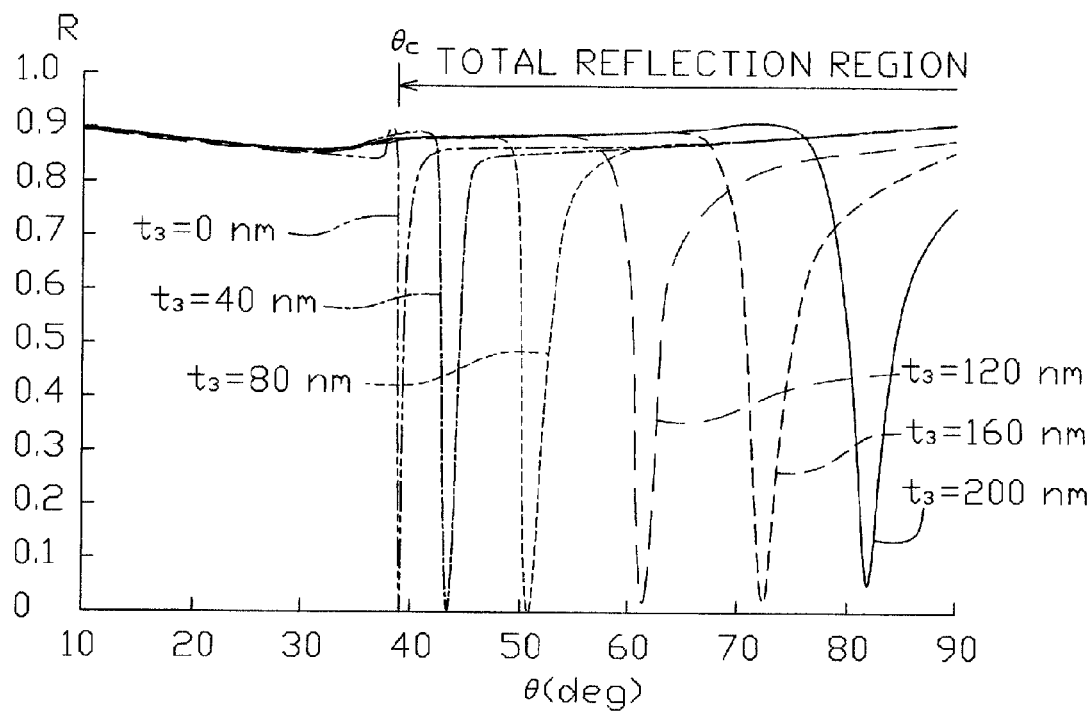

Fig. 24

| METAL | GOLD (Au) | PLATINUM (Pt) |
|---|---|---|
| GRAIN SIZE (g) | 60 nm | 12 nm |
| RELATIVE BACKGROUND LIGHT | 600 | 1 |

LIGHT SCATTERING TYPE PARTICLE DETECTOR USING SCATTERED LIGHT OF SURFACE PLASMON RESONANCE PHOTONS

This application claims the priority benefit under 35 U.S.C. §119 to Japanese Patent Application Nos. JP2010-272404 and JP2011-250329 filed on Dec. 7, 2010, and Nov. 16, 2011, respectively, which disclosures are hereby incorporated in their entirety by reference.

BACKGROUND

1. Field

The presently disclosed subject matter relates to a light scattering type particle detector.

2. Description of the Related Art

In a semiconductor manufacturing apparatus where the high integration and the fine structure have been enhanced, absorbed particles affecting the manufacturing yield have been reduced in size. Also, even in a medicine manufacturing apparatus or a food manufacturing apparatus, since bacteria are easily absorbed on particles floating in the air, a highly-purified environment has been required. In the semiconductor manufacturing apparatus, the medicine manufacturing apparatus and the food manufacturing apparatus, a highly-purified space, i. e., a clean room excluding fine particles as many as possible is required. Such a clean room is monitored by an easily-operated particle detector for detecting fine particles in real time. Particularly, ultra pure water requires an extremely high purifying degree where the number of fine particles whose diameter is less than 0.1 μm is not larger than 1/mL. Particle detectors of a light scattering type for detecting fine particles in the air or in water have been known, and a halogen lamp, a helium-neon (He—Ne) laser, a semiconductor laser diode (LD), an LD-excited solid state laser or the like is used as a light source for such particle detectors.

As illustrated in FIG. 25, which illustrates a first prior art light scattering type particle detector (see: FIG. 2 of Takashi MINKAMI, "Fine Particle Meter Using LD-Excited Solid-State Laser as Light Source", Oct. 2001), this particle detector is a laser oscillator including a gas laser medium source such as He—Ne laser source 101, and mirrors 102 and 103 provided on both sides of the He—Ne laser source 101, wherein a particle detecting region 104 is provided. Since the strength of an electric field within the laser oscillator which depends upon the reflectivities of the mirrors 102 and 103 is as large as about 100 to 1000 times the strength of an electric field outside of the laser oscillator, the strength of scattered light SL scattered by fine particles passing through the particle detecting region 104 becomes very large. Therefore, such fine particles passing through the particle detecting region 104 at a flow rate of 300 mL/min, for example, can be detected by detecting the scattered light SL.

The above described first prior art particle detector, however, has the following problems:

(1) Since the He—Ne laser source 101 is formed by a glass tube, the He—Ne laser source 101 is small in mechanical strength, large in size, and short in life-time, thus increasing the size and manufacturing cost of the first prior art particle detector.

(2) In order to maintain the alignment stability of the laser oscillator, the laser oscillator has to be provided under a finely-temperature-controlled vibration removing environment, which would further increase the size and manufacturing cost of the first prior art particle detector.

(3) When air or water passes through the particle detecting region 104, turbulent flow and fluctuation of temperature would invite fluctuation of an optical path length of the laser oscillator due to the change of the refractive index of the laser oscillator, thus drastically changing the strength of oscillation of the laser oscillator to destabilize the detection of fine particles.

(4) The principle of light scattering is based upon Rayleigh scattering whose scattering cross section S is represented by $$S \propto d^6 \cdot \lambda^4 \quad (1)$$

where "d" is a diameter of fine particles; and
λ is a wavelength of light of the laser oscillator.

Therefore, although fine particles with a diameter "d" of about 0.5 μm at most to increase their scattering cross section S can be detected, it is difficult to detect fine particles with a diameter of less than about 0.1 μm to decrease their scattering cross section S.

As illustrated in FIG. 26, which illustrates a second prior art light scattering type particle detector (see: FIG. 3 of Takashi MINAKAMI, "Fine Particle Meter Using LD-Excited Solid-State Laser as Light Source", Oct. 2001, JP2002-151765A, JP2002-223019A and (US2004/001974A1), an laser-diode (LD)-excited solid-state laser oscillator is constructed by an LD device 201 as an exciting light source, a condensing lens 202, a solid-state laser such as a $Nd^{3+}:YVO_4$ laser crystal 203, and mirrors 204 and 205, wherein a particle detecting region 206 is provided. Since the strength of an electric field within the LD-excited laser oscillator which depends upon the reflectivities of the mirrors 204 and 205 is large about 100 to 1000 times as the strength of an electric field outside of the LD-excited laser oscillator, the strength of scattered light SL by fine particles passing through the particle detecting region 206 becomes very large. Therefore, such fine particles passing through the particle detecting region 206 at a flow rate of 300 mL/mm, for example, can be detected by detecting the scattered light SL.

The above described second prior art particle detector has the following advantage over the above-mentioned first prior art particle detector. That is, since the solid-state crystal 203 is large in mechanical strength, small in size, and long in life-time, thus decreasing the size and manufacturing cost of the second prior art particle detector.

The above-described second prior art particle detector, however, still has the following problems:

(1) In order to maintain the alignment stability of the LD-excited laser oscillator, the LD-excited laser oscillator has to be provided under a finely-temperature controlled vibration removing environment, which would still increase the size and manufacturing cost of the second prior art particle detector.

(2) When air or water passes through the particle detecting region 206, turbulent flow and fluctuation of temperature would invite fluctuation of an optical path length of the ID-excited laser oscillator due to the change of the refractive index of the LD-excited laser oscillator, thus drastically changing the strength of oscillation of the LD-excited Laser oscillator to destabilize, the detection of fine particles.

(3) The principle of light scattering is based upon Rayleigh scattering whose scattering cross section S is based upon the above mentioned formula (1). Therefore, it is still difficult to detect fine particles with a diameter of less than about 0.1 μm to decrease their scattering cross section S.

SUMMARY

The presently disclosed subject matter seeks to solve one or more of the above-described problems.

According to the presently disclosed subject matter, a particle detector includes a light source, and a metal layer having an incident/reflective surface. Incident light from the light source reaches the incident/reflective surface to excite near-field surface plasmon resonance photons at the photoelectric surface. A particle deposited on the photoelectric surface of the metal layer changes the near filed surface plasmon resonance photons to far-field scattered light. The particle detector further includes a scattered light detecting unit, provided above the photoelectric surface of the metal layer, for detecting the far-field scattered light. Thus, fine particles with a diameter of less than about 0.1 µm can be detected due to the electric field enhancing effect and the wavelength reducing effect by surface plasmon resonance photons.

Also, the particle detector according to the presently disclosed subject matter further includes a dielectric protection layer provided on the photoelectric surface of the metal layer, thus preventing the metal layer from being flawed.

According to the presently disclosed subject matter, the alignment stability can be improved to thereby decrease the size and manufacturing cost. Particularly, fine particles with a diameter of less than about 0.1 µm can be stably and easily detected.

BRIEF DESCRIPTION OF THE DRAWINGS

The above and other objects, advantages and features of the presently disclosed subject matter will be more apparent form the following description of certain preferred embodiments, as compared with the prior art, taken in conjunction with the accompanying drawings, wherein:

FIGS. 5A, 5B, 5C and 5D are electric field strength diagrams for explaining the optimum incident angle $\theta_{opt}$ of FIGS. 4A and 4B;

FIG. 10 is an ATR signal spectrum diagram for explaining selection of the thickness $t_2'$ of the AG layer at step 901 of FIG. 9;

FIG. 13 is an ATR signal spectrum diagram for explaining selection of the thickness $t_3$ of the SiO$_2$ protection layer at step 903 of FIG. 9;

FIG. 24 is a table showing a relationship between the size of grains and relative background light strength of metals;

DETAILED DESCRIPTION OF EXEMPLARY EMBODIMENTS

Figure 1:
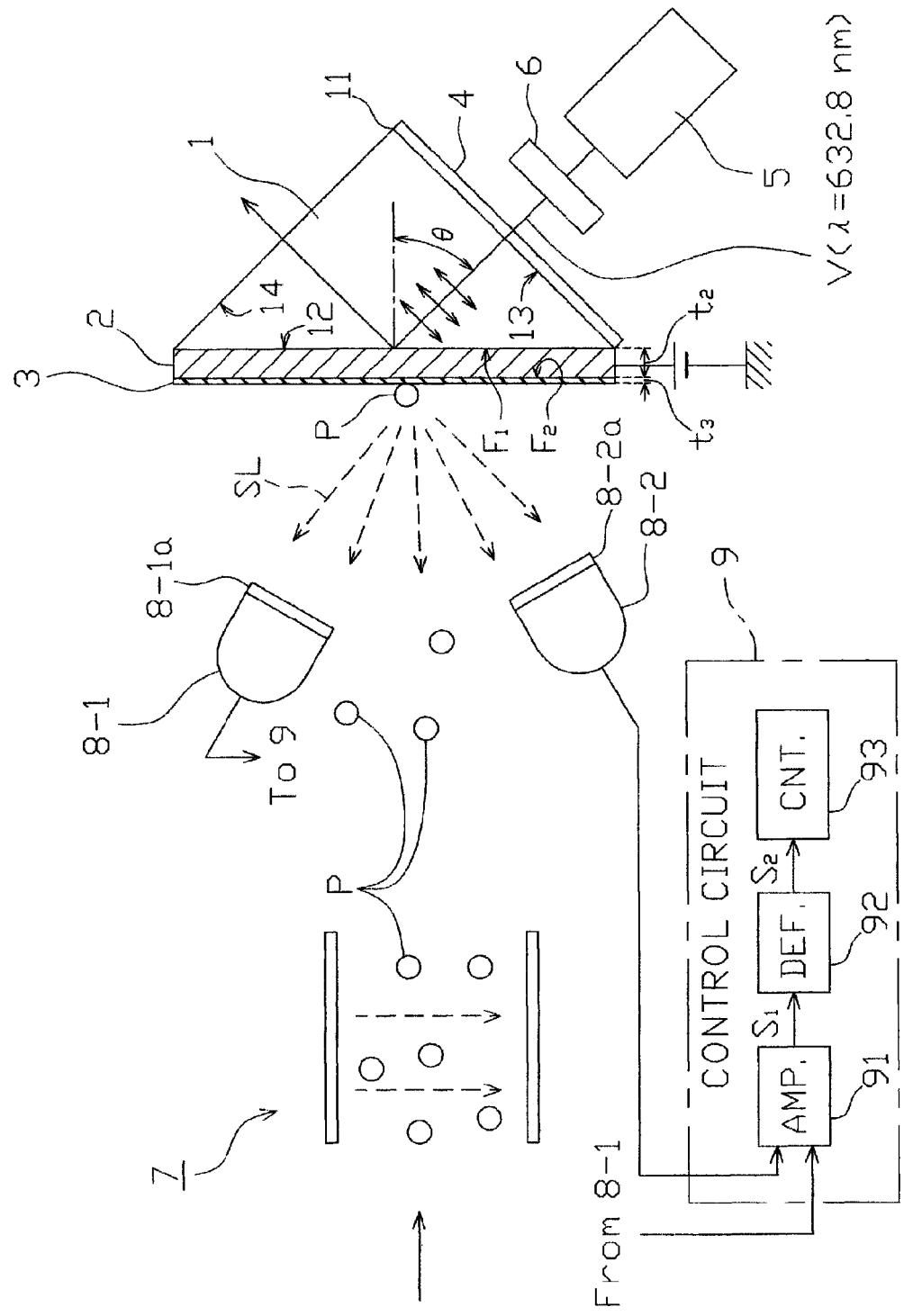
FIG. 1 is a partly cross-sectional view illustrating a first embodiment of the particle detector according to the presently disclosed subject matter.

In FIG. 1, which illustrates a first embodiment of the particle detector according to the presently disclosed subject matter, this particle detector is constructed by a common glass prism or a BK-7 prism 1 as a transparent body for a visible laser ray with a refractive index $n_1$ of 1.535 and a vertical angle of 90°, a gold (Au) layer 2 as a metal layer deposited by an evaporating process or a sputtering process on a surface 12 of the BK-7 prism 1 opposing an arris 11 thereof, and a silicon dioxide (SiO$_2$) layer 3, for example, as a dielectric layer deposited on a photoelectric surface $F_2$ of the AU layer 2 opposing an incident/reflective surface $F_1$ thereof.

The Au layer 2 is about 1 cm long, and its thickness $t_2$ is selected within about 10 nm to 10 µm. If the thickness $t_2$ of the Au layer 2 is smaller than 10 nm, the Au layer 2 cannot sufficiently absorb evanescent photons generated therein. On the other hand, if the thickness $t_2$ of the Au layer 2 is larger than 10 µm, the generation of evanescent photons in the Au layer 2 is attenuated, so as not to excite surface plasmon resonance (SPR) photons in the Au layer 2.

Note that an about 1 to 2 nm thick metal layer made of Cr or the like may be deposited on the surface of the BK-7 prism 1 to enhance the contact characteristics between the Au layer 2 and the BK-7 prism 1.

An anti reflection (AR) coating layer 4 is coated on a surface 13 of the BK-7 prism 1. In this case, the arris 11 of the BK-7 prism 1 is formed by the surface 13 as well as a surface 14. Note that, if the incident loss by the reflectivity such as 8% of the BK-7 prism 1 is negligible, the AR coating layer 4 can be omitted.

Further, a He—Ne laser source 5 and a wavelength plate 6 are provided. As a result, the visible laser ray V whose wavelength λ is 632.8 nm is emitted from the He—Ne laser source 5 and is incident via the wavelength plate 6, the AR coating layer 4 and the BK-7 prism 1 to the Au layer 2. In this cause, in order to generate evanescent photons in the Au layer 2, the rotational angle of the wavelength plate 6 can be adjusted, so that the visible laser ray V incident to the Au layer 2 is polarized, i. e., TM-polarized or P-polarized in parallel with the incident/reflective surface $F_1$ of the Au layer 2.

Note that, since the visible laser ray V is linearly-polarized, the rotational angle of the He—Ne laser source 5 can be adjusted without provision of the wavelength plate 6 to emit the above-mentioned P polarized light.

Note that, SPR photons are generated by irradiating the Au layer 2 with the visible laser ray V of the He—Ne laser source 5; however, since the wavelength of light capable of exciting SPR photons by the Au layer 2 is ranged from about 500 nm to 2000 nm, other light sources than the He—Ne laser source 5 can be used. In this case, a wavelength of a visible light region close to the SPR wavelength 500 nm of Au is preferable to detect fine particles P in view of the wavelength reduction effect.

Also, instead of the high directivity and high coherent laser light, inexpensive monochromatic light sources such as light emitting diodes (LEDs) can be used to emit monochromatic light which would exhibit almost the same effect as the laser light by a suitable optical design in consideration of the directivity and deflection characteristics.

An ionizer 7 charges fine particles P with a negative potential, while a positive voltage is applied to the Au layer 2. Therefore, charged fine particles P are accelerated to be deposited on the $SiO_2$ protection layer 3 on the photoelectric surface $F_2$ of the Au layer 2, and are subject to a surface plasmon field. Note that, the ionizer 7 can charge fine particles P with a positive potential, while a negative voltage is applied to the Au layer 2, to obtain the same phenomenon. In other words, the polarity sign of charges at the fine particles P is opposite to the polarity sign of a voltage applied to the Au layer 2. As a result, the above-mentioned near-field SPR photons excited on the Au layer 2 are changed by the fine particles P deposited on the $SiO_2$ protection layer 3 to far field scattered light SL. Then, a photoelectric conversion is performed upon the scattered light SL by photomultiplier tubes 8-1 and 8-2 (scattered light detecting means) associated with interference filters 8-1a and 8-2a, and output signals of the photomultiplier tubes 8-1 and 8-2 are supplied to a control circuit 9. In this case, the interference filters 8-1a and 8-2a are operated to pass only light at a predetermined frequency band. Since the frequency of the scattered light SL is the same as that of incident light, and therefore, the predetermined frequency band of the interference filters 8-1a and 8-2a is selected to include the frequency of the visible laser ray V of the He—Ne laser source 5. Note that, the number of photomultipliers can be one, or more than two.

Also, if the scattered light SL is expected to be detected in the periphery of locations where SPR photons are generated, one or more optical waveguides are provided closer to such locations to collect and guide the SPR photons which would be detected by one photomultiplier connected to the optical waveguides. That is, the scattered light SL generated at a plurality of locations can be detected by only one photomultiplier, which would decrease the size and manufacturing cost of the particle detector of FIG. 1.

The control circuit 9 is constructed by an amplifier 91 for adding and amplifying the output signals of the photomultiplier tubes 8-1 and 8-2, a differentiator 92 for differentiating the output signal $S_1$ of the amplifier 91, and a pulse height discriminating counter 93 for counting the pulse output signal $S_2$ of the differentiator 92. That is, the pulse height discriminating counter 93 includes a plurality of individual counter units each for counting the number of pulse output signal $S_2$ in accordance with their pulse heights. Note that the control circuit 9 can be constructed by a microcomputer which includes programs for carrying out the functions of the differentiator 92 and the pulse-height discriminating counter 93.

The operational principle of the particle detector of FIG. 1 uses the electric field enhancing effect and the wavelength reducing effect of SPR photons. Regarding the surface plasmon resonance (SPR) photons, reference is made to Heinz Raether, "Surface Plasmons on Smooth and Rough Surfaces and on Gratings", Springer-Verlag Berlin Heidelberg New York, pp. 16-19, 1988.

That is, evanescent photons are generate din the Au layer 2 by the visible laser ray V to excite photons on the photoelectric surface $F_2$ of the Au layer 2. In this case, since the visible laser ray V is P-polarized, the visible laser ray V has an electric field component in parallel with the surface of the Au layer 2 and another electric field perpendicular to the surface of the Au layer 2, so that the respective electric fields are amplified. For example, the intensity of the electric field of light incident to the Au layer 2 is made to be about ten times by the SPR photons generated therein. Therefore, since the intensity of the light incident to the Au layer 2 is represented by the square of the value of the electric field, the light incident to the Au layer 2 is amplified by about 100 (=10×10) times. That is, the strength of the scattered light SL by the fine particles P is increased by about 100 times by the electric field enhancing effect of SPR photons.

Simultaneously, the wavelength of SPR photons generated in the Au layer 2 is reduced by about $\frac{1}{10}$ to $\frac{1}{100}$ with respect to the wavelength of the visible laser ray V due to the wavelength reducing effect of SPR photons. As a result, the scattering cross section S of the scattered light SL is increased to $(\frac{1}{10})^{-4}$ through $(\frac{1}{100})^{-4}$ (see the formula (1)), that is, the strength of the scattered light SL can be increased to $10^4$ through $10^8$.

Thus, in view of the electric field enhancing effect and the wavelength reducing effect of SPR photons, the scattered light enhancing effect of $10^6$ to $10^{10}$ times can be expected as compared with the prior art particle detectors. Therefore, even if the term $d^6$ in the formula (1) is decreased, it is possible to detect fine particles P with a diameter of less than 0.1 μm.

Figure 2:
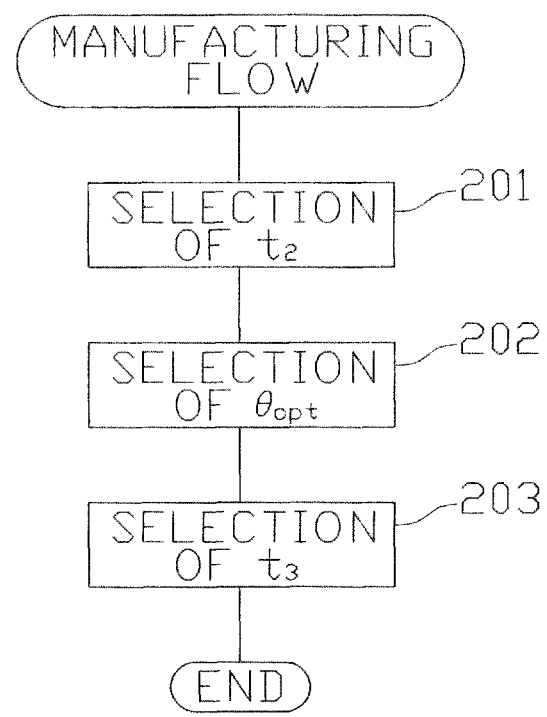
FIG. 2 is a flowchart for illustrating a manufacturing flow of the particle detector of FIG. 1.

FIG. 2 is a flowchart for explaining a manufacturing flow of the particle detector of FIG. 1.

First, at step 201, an optimum thickness $t_2$ of the Au layer 2 is selected. That is, if the incident angle θ of the visible laser ray V at the incident/reflective surface $F_1$ of the Au layer 2 is an optimum incident angle $θ_{opt}$ (>$θ_c$ where $θ_c$ is a critical angle), the number of SPR photons excited on the photoelectric surface $F_2$ of the Au layer 2 of FIG. 1 is maximum. In other words, when $θ=θ_{opt}>θ_c$, the reflectivity R at the incident/reflective surface $F_1$ of the Au layer 2 is minimum. In this case, FIG. 3 was obtained by a simulation which calculates a reflectivity R of light reflected form the incident/reflective surface $F_1$ of the Au layer 2 by angularly scanning the BK-7 prism 1 with the visible laser ray V. This simulation can be carried out by the simulation software WinSpall (trademark) developed by Max Planck Institute.

Figure 3:
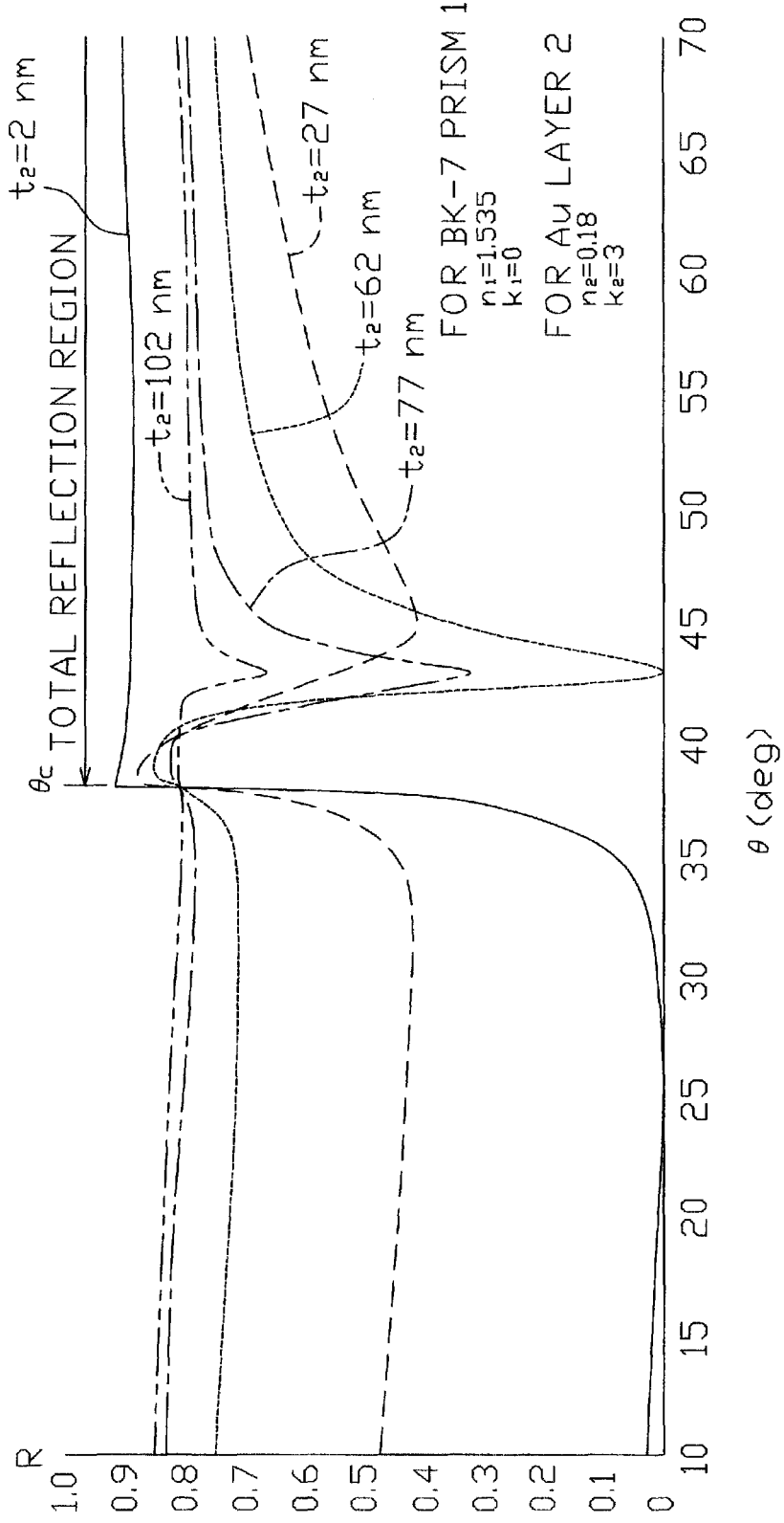
FIG. 3 is an attenuated total reflection (ART) signal spectrum diagram for explaining selection of the thickness $t_2$ of the Au layer at step 201 of FIG. 2.

In FIG. 3, the simulation conditions under the wavelength $\lambda=632.8$ nm of the visible laser ray V are as follows:
(1) For the BK-7 prism 1,
  the refractive index $n_1$ is 1.535; and
  the extinction coefficient $k_1$ is 0.
(2) For the Au layer 2,
  the refractive index $n_2$ is 0.18;
  the extinction coefficient $k_2$ is 3; and
  the thickness $t_2$ is variable.
(3) For the SiO$_2$ protection layer 3,
  the thickness $T_3$ is 0.

That is, the SiO$_2$ protection layer 3 is assumed to be absent.

In FIG. 3, only one ATR signal spectrum of the Au layer 2 whose thickness $t_2$ is 53 nm is selected from a plurality of ATR signal spectrums of the Au layer 2 whose thickness $t_2$ is variable, i. e., 2 nm, 27 nm, 62 nm, 77 nm and 102 nm. That is, the ATR signal spectrum of FIG. 3 shows that, if the thickness $t_2$ of the Au layer 2 is smaller than 10 nm, the Au layer 2 cannot sufficiently absorb evanescent photons generated therein, and if the thickness $t_2$ of the Au layer 2 is larger than 60 nm, the generation of evanescent photons in the Au layer 2 is attenuated, so as not to excite SPR photons in the Au layer 2, this increasing the reflectivity at a plasmon dip. Although not illustrated in FIG. 3, from FIG. 4A, the ATR signal spectrum at $t_2=53$ nm shows a sharp plasmon dip where the reflectivity R is 0. Therefore, the thickness $t_2$ of the Au layer 2 is selected to be 53±1 nm, so that the excited SPR photons are maximum.

Figure 4A:
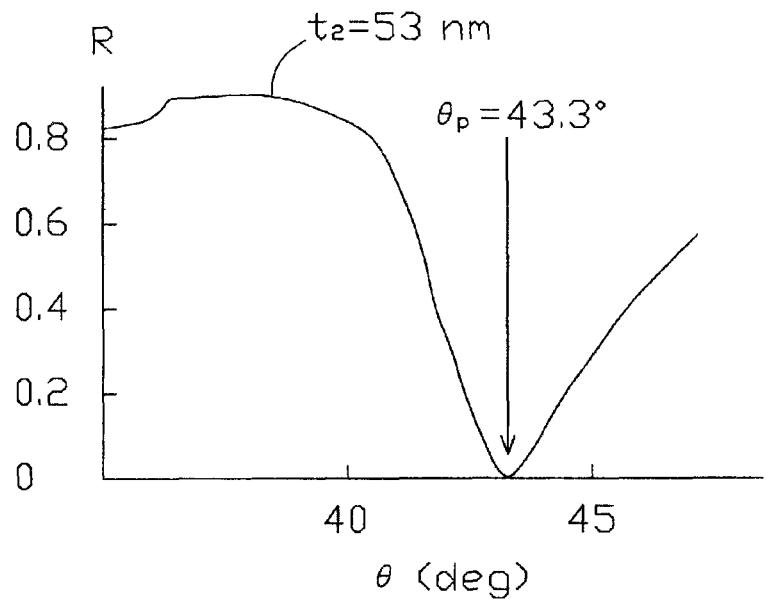
FIGS. 4A and 4B are an ATR signal spectrum diagram and an electric field strength diagram, respectively, for explaining selection of the optimum incident angle $\theta_{opt}$ at step 202 of FIG. 2.
Figure 4B:
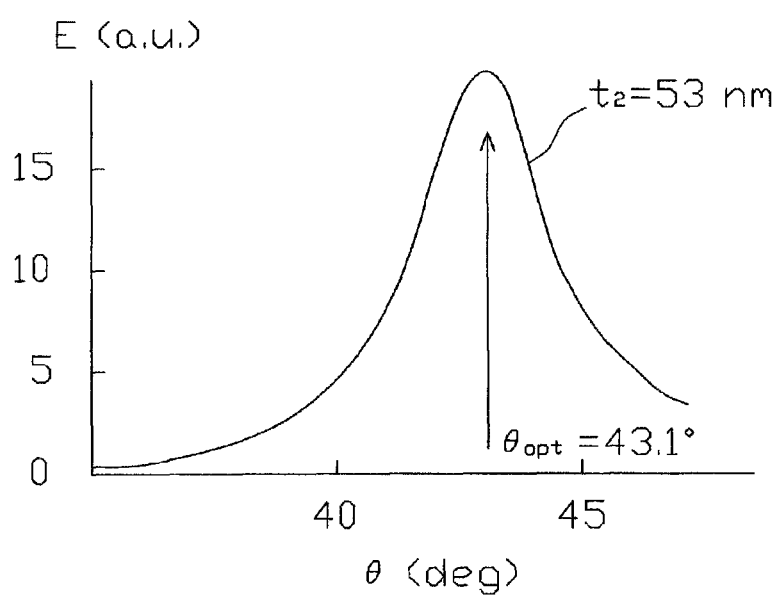

Next, at step 202, an optimum incident angle $\theta_{opt}$ is selected. As illustrated in FIG. 4A, when the incident angle $\theta$ is a plasmon dip angle $\theta_p$ (=43.3°), the excited SPR photons are maximum. However, as illustrated in FIG. 4B, the electric field strength E is maximum when the incident angle $\theta=43.1°$ which is a little smaller than the plasmon dip angle $\theta_p$ (=43.3°). Therefore, in order to exhibit the electric field strength enhancing effect by the SPR photons, the optimum incident angle $\theta_{opt}$ is selected at 43.1°. In this case, the electric field strength E is enhanced by about 20 times that of the incident light.

As illustrated in FIGS. 5A, 5B, 5C and 5D, when the thickness $t_2$ of the Au layer 2 is 0 nm or 20 nm smaller than 53 nm, or 80 nm larger 53 nm even if the incident angle $\theta$ is at the optimum incident angle $\theta_{opt}$, the excited SPR photons are smaller and the full-width of half maximum of the electric field strength E is larger, so that the enhancement of the electric field strength E is much smaller than about 20 times of incident light.

Figure 6:
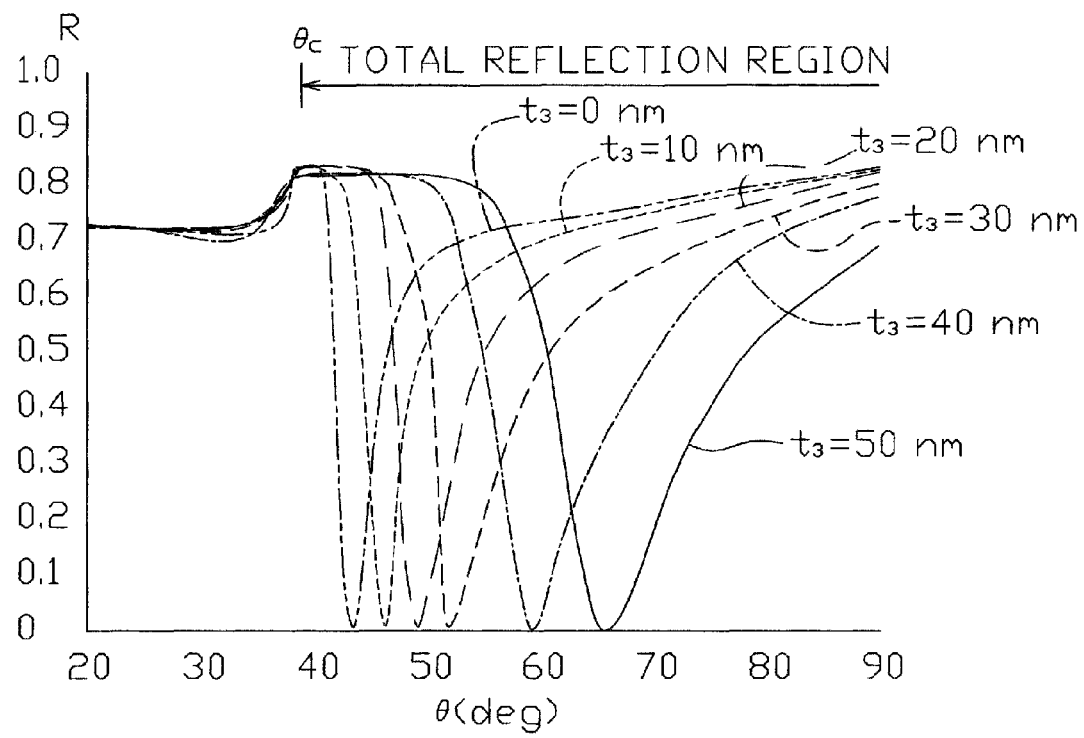
FIG. 6 is an ATR signal spectrum diagram for explaining selection of the thickness $t_3$ of the SiO$_2$ protection layer at step 203 of FIG. 2.

Next, at step 203, an optimum thickness $t_3$ of the SiO$_2$ protection layer 3 is selected. FIG. 6 was obtained by a simulation using the above-mentioned simulation software WinSpall (trademark) which calculates a reflectivity R of light reflected from the incident/reflective surface $F_1$ of the Au layer 2 where the thickness $t_2$ of the Au layer 2 is fixed at 53 nm while the thickness $t_3$ of the SiO$_2$ protection layer 3 is changed from 0 to 50 nm. In order to simplify the description, only six ATR signal spectrums at $t_3=0$ nm, 10 nm, 20 nm, 40 nm and 50 nm are illustrated in FIG. 6.

In FIG. 6, the simulation conditions under the wavelength $\lambda=632.8$ nm of the visible laser ray V are as follows:
(1) For the BK-7 prism 1.
  the refractive index $n_1$ is 1.535: and
  the extinction coefficient $k_1$ is 0,
(2) For the Au layer 2,
  the thickness $t_2$ is 53 nm;
  the refractive index $n_2$ is 0.18: and
  the extinction coefficient $k_2$ is 3.
(3) For the SiO$_2$ protection layer 3,
  the thickness $t_3$ is variable;
  the refractive index $n_3$ is 1.5: and
  the extinction coefficient $k_3$ is 0.

As shown in FIG. 6, since the SiO$_2$ protection layer 3 has no absorption loss ($k_3=0$), when the thickness $t_3$ of the SiO$_2$ protection layer 3 is increased, the plasmon dip angle is shifted toward a higher angle where the depth of the plasmon dip is at a point of R=0, so that SPR photons can be excited regardless of the thickness $t_3$ of the SiO$_2$ protection layer 3. In this case, the narrower the full-width at half maximum of the plasmon dip, the larger the electric field strength E. Therefore, in order to increase the strength of the scattered light SL from the fine particles P, the SiO$_2$ protection layer 3 would be unnecessary. However, the fine particles P are generally composed of human skin, fiber, resist residue, metal slug and so on, whose material, refractive index and shape are variegated. On the contrary, if the refractive index of the fine particles P is close to that of the SiO$_2$ protection layer 3, photoenergy of the SPR photons is resonantly-tunneled to the fine particles P to enhance the strength of the scattered light SL. Therefore, in view o these two circumstances, the thickness $t_3$ of the SiO$_2$ protection layer 3 is selected to prevent the Au layer 2 from being flawed.

The operation of the control circuit 9 of FIG. 1 is explained next with reference to FIGS. 7A and 7B.

Figures 7A, 7B:
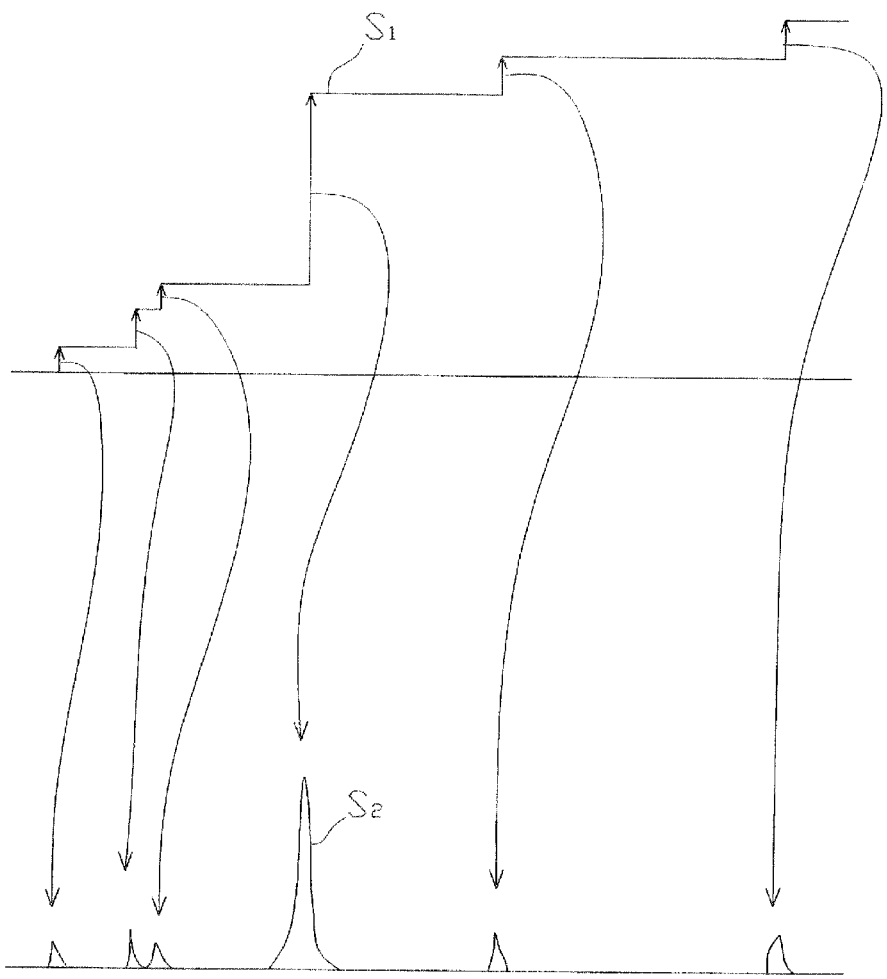
FIGS. 7A and 7B are timing diagrams for explaining the operation of the control circuit of FIG. 1.

That is, as illustrated in FIG. 7A, every time one charged fine particle P is deposited on the SiO$_2$ protection layer 3, scattered light SL by that charged fine particle P is accumulated in the amplifier 91, so that the output signal $S_1$ of the amplifier 91 is accumulated by that charged fine particle P. At this time, the increase amount of the output signal $S_1$ corresponds to the diameter "d" of that deposited fine particle P. Therefore, as illustrate din FIG. 7B, each pulse-height of the output signal $S_2$ of the differentiator 92 corresponds to the diameter "d" of that deposited fine particle P. As a result, each of the individual counter units of the pulse-height discriminating counter 93 counts the number of deposited fine particles P in accordance with their diameter "d", i. e., their pulse heights. Thus, the densities of deposited fine particles P can be calculated in accordance with the diameter "d" thereof.

In the control circuit 9 where the above-mentioned operation is completed, every time all the fine particles P deposited on the SiO protection layer 3 are removed or the entirety of the BK-7 prism 1, the Au layer 2 and the SiO$_2$ protection layer 3 are replaced by new ones, the output signal $S_1$ of the amplifier 91 is reset or initialized.

Figure 8:
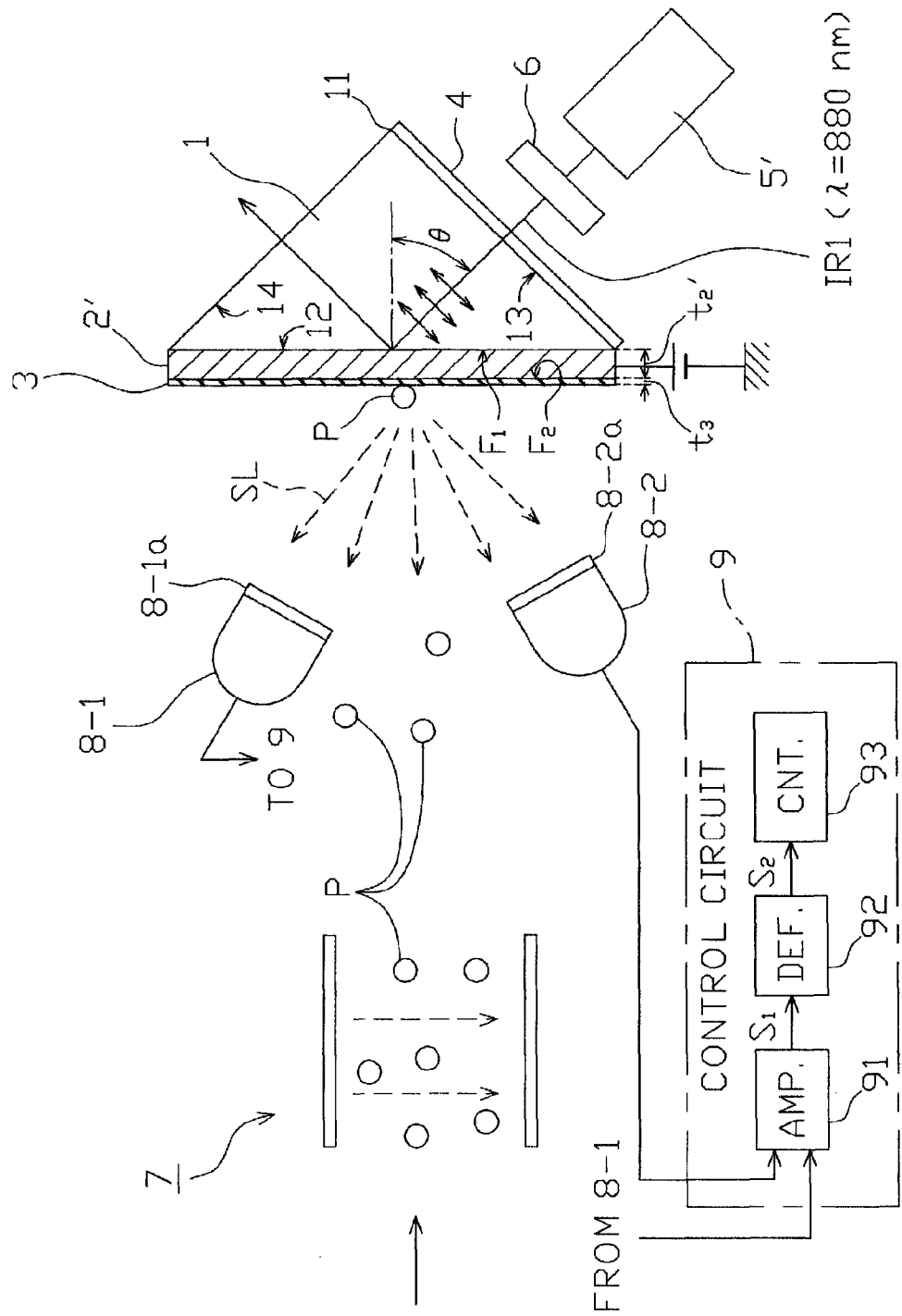
FIG. 8 is a partly cross-sectional view illustrating second embodiment of the particle detector according to the presently disclosed subject matter.

In FIG. 8, which illustrates a second embodiment of the particle detector according to the presently disclosed subject matter, a silver (Ag) layer 2' as a metal layer is deposited by an evaporating process or a sputtering process on the surface 12 of the BK-7 prism 1, instead of the Au layer 2 of FIG. 1, and an infrared laser source 5' for emitting an infrared laser ray IR1 whose wavelength $\lambda$ is 880 nm, instead of the He—Ne laser source 5 of FIG. 1.

In the same way as the Au layer 2 of FIG. 1, the Ag layer 2' is about 1 cm long, and its thickness $t_2'$ is selected within about 10 nm to 10 μm. Also, an about 1 to 2 nm thick metal layer made of Cr or the like may be deposited on the surface of the BK-7 prism 1 to enhance the contact characteristics between the Ag layer 2' and the BK-7 prism 1.

Note that, SPR photons are generated by irradiating the Ag layer 2' with the infrared laser ray IR1 of the infrared laser source 5'; however, since the wavelength of light capable of exciting SPR photons by the Ag layer 2' is ranged from about 340 nm to 2000 nm, other light sources than the infrared laser source 5' can be used. In this case, a wavelength of an infrared light region close to the SPR wavelength 340 nm of Ag is preferable to detect fine particles P in view of the wavelength reducing effect.

Also, instead of the high directivity and high coherent laser light, inexpensive monochromatic light sources such as light emitting diodes (LEDs) can be used to emit monochromatic light which would exhibit almost the same effect as the laser light by a suitable optical design in consideration of the directivity and deflection characteristics.

The operational principle of the particle detector of FIG. 8 is the same as that of the particle detector of FIG. 1 which uses the electric field enhancing effect and the wavelength reducing effect of SPR photons.

Figure 9:
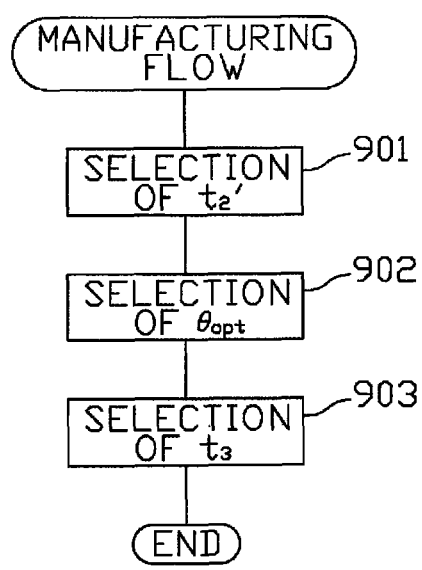
FIG. 9 is a flowchart for illustrating a manufacturing flow of the particle detector of FIG. 8.

FIG. 9 is a flowchart for explaining a manufacturing flow of the particle detector of FIG. 8.

First, at step 901, an optimum thickness $t_2'$ of the Ag layer 2' is selected. That is, if the incident angle θ of the infrared laser ray IR1 at the incident/reflective surface $F_1$ of the Ag layer 2' is an optimum incident angle $\theta_{opt}$ ($>\theta_c$ where $\theta_c$ is a critical angle), the number of SPR photons excited on the photoelectric surface $F_2$ of the Ag layer 2' of FIG. 8 is maximum. In other words, when $\theta=\theta_{opt}>\theta_c$, the reflectivity R at the incident/reflective surface $F_1$ of the Ag layer 2' is minimum. In this case, FIG. 10 was obtained by a simulation which calculates a reflectivity R of light reflected form the incident/reflective surface $F_1$ of the Ag layer 2' by angularly scanning the BK-7 prism 1 with the infrared laser ray IR1. This simulation can be carried out by the simulation software WinSpall (trademark) developed by Max Planck Institute.

In FIG. 10, the simulation conditions under the wavelength λ=880 nm of the infrared laser ray IR1 are as follows:
(1) For the BK-7 prism 1,
the refractive index $n_1$ is 1.535: and
the extinction coefficient $k_1$ is 0.
(2) For the Ag layer 2',
the refractive index $n_2'$ is 0.163;
the extinciton coefficient $k_2'$ is 6: and
the thickness $t_2'$ is variable.
(3) For the $SiO_2$ protection layer 3,
the thickness $t_3$ is 0.

That is, the $SiO_2$ protection layer 3 is assumed to be absent.

In FIG. 10, only one ATR signal spectrum of the Ag layer 2' whose thickness $t_2'$ is 42 nm is selected from a plurality of ATR signal spectrums of the Ag layer 2' whose thickness $t_2'$ is variable, i. e., 2 nm, 22 nm, 42 nm, 62 nm, 82 nm and 102 nm. That is, the ATR signal spectrum of FIG. 10 shows that, if the thickness $t_2'$ of the Ag layer 2' is smaller than 22 nm, the Ag layer 2' cannot sufficiently absorb evanescent photons generated therein, and if the thickness $t_2'$ of the Ag layer 2' is larger than 62 nm, the generation of evanescent photons in the Ag layer 2' is attenuated, so as not to excite SPR photons in the Ag layer 2', thus increasing the reflectivity at a plasmon dip. Although not illustrated in FIG. 10, from FIG. 11A, the ATR signal spectrum at $t_2'$=42 nm shows a sharp plasmon dip where the reflectivity R is 0. Therefore, the thickness $t_2'$ of the Ag layer 2' is selected to be 42±1 nm, so that the excited SPR photons are maximum.

Figure 11A:
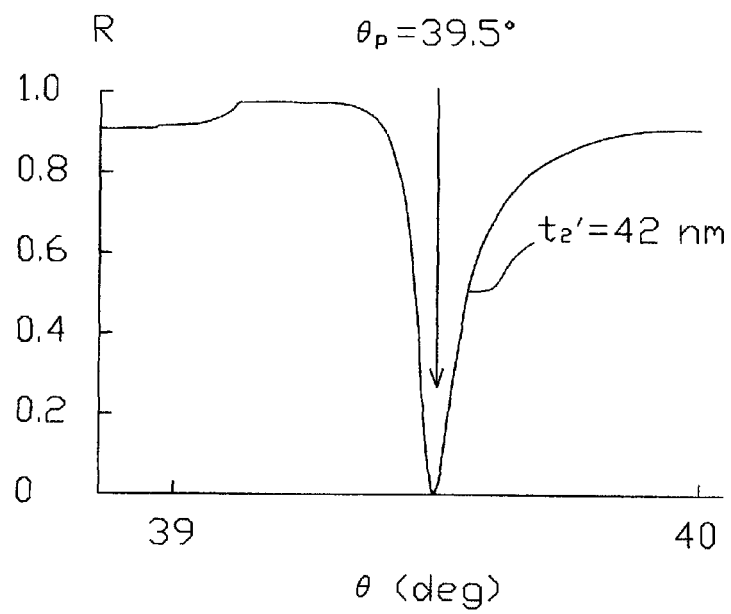
FIGS. 11A and 11B are an ATR signal spectrum diagram and an electric field strength diagram, respectively, for explaining selection of the optimum incident angle $\theta_{opt}$ at step 902 of FIG. 9.
Figure 11B:
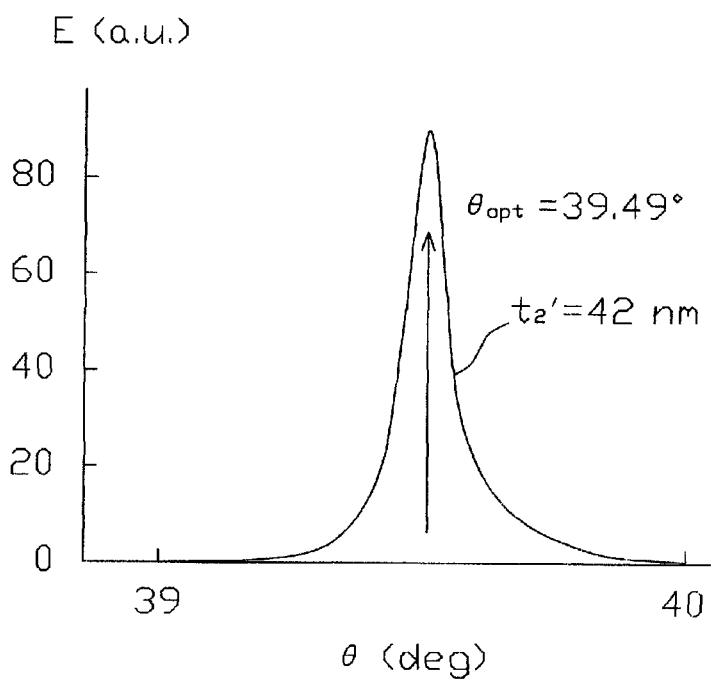
Figure 12A:
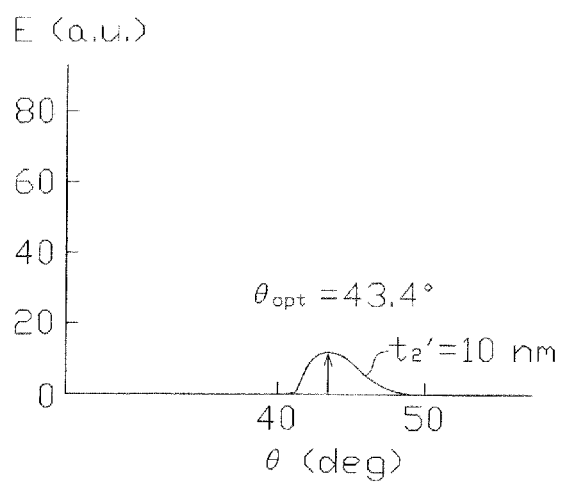
FIGS. 12A, 12B, 12C and 12D are electric field strength diagrams for explaining the optimum incident angle $\theta_{opt}$ of FIGS. 11A and 11B.
Figure 12B:
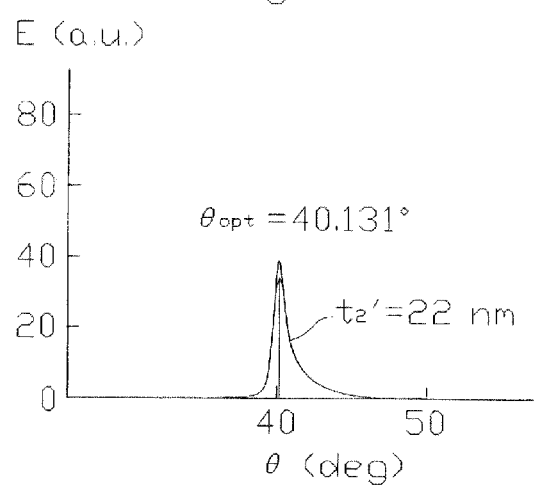
Figure 12C:
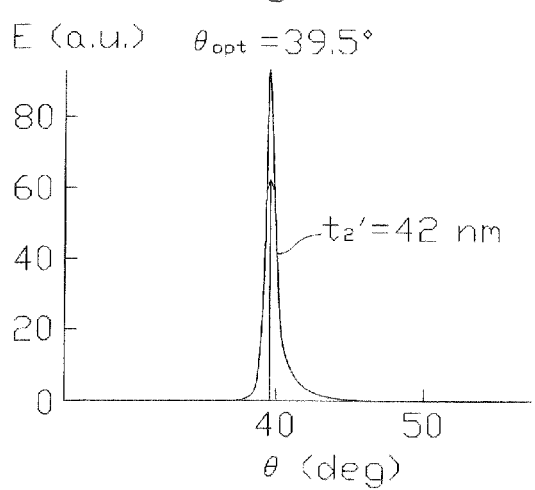
Figure 12D:
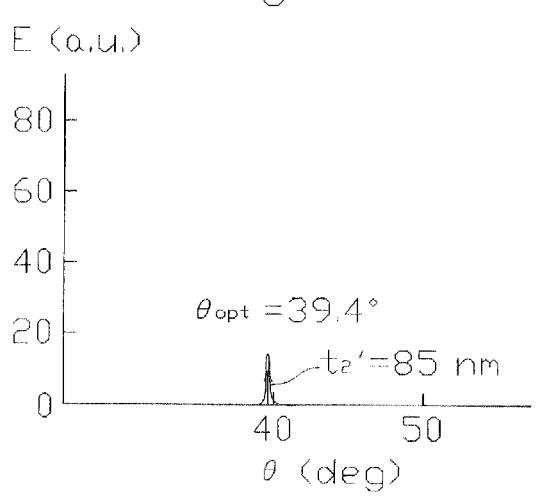
Figure 14A:
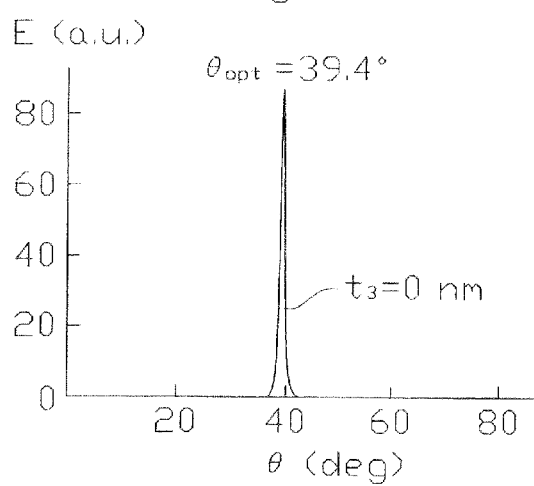
FIGS. 14A, 14B, 14C and 14D are electric field strength diagrams for explaining the optimum incident angle $\theta_{opt}$ of FIG. 13.
Figure 14B:
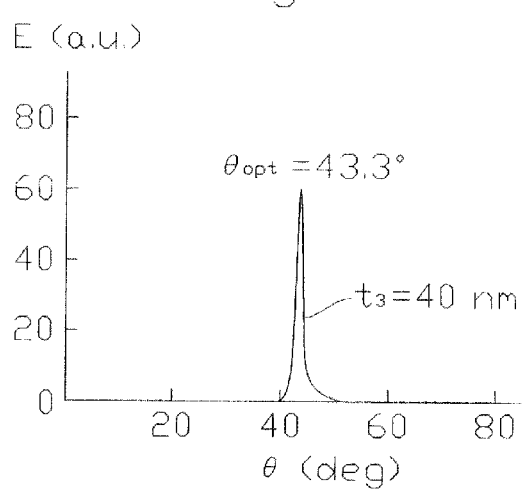
Figure 14C:
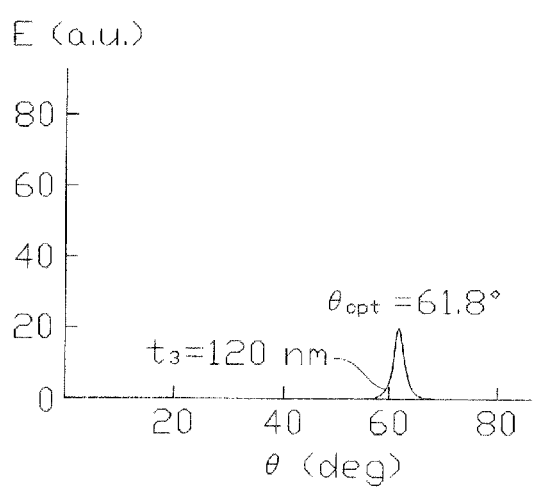
Figure 14D:
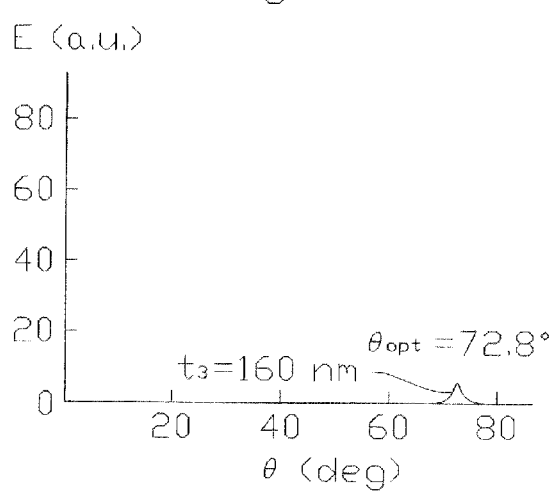

Next, at step 902, an optimum incident angle $\theta_{opt}$ is selected. As illustrated in FIG. 11A, when the incident angle θ is a plasmon dip angle $\theta_p$ (=39.5°), the excited SPR photons are maximum. However, as illustrated in FIG. 11B, the electric field strength E is maximum when the incident angle θ=39.49° which is a little smaller than the plasmon dip angle $\theta_p$ (=39.5°). Therefore, in order to exhibit the electric field strength enhancing effect by the SPR photons, the optimum incident angle $\theta_{opt}$ is selected at 39.49°. In this case, the electric field strength E is enhanced by about 90 times that of the incident light. This larger enhancement of the electric field strength of the second embodiment than that of the first embodiment is due to the difference in extinction coefficient between the Ag layer 2' and the Au layer 2.

As illustrated in FIGS. 12A, 12B, 12C and 12D, when the thickness $t_2'$ of the Ag layer 2' is 10 nm or 22 nm smaller than 42 nm, or 85 nm larger 42 nm even if the incident angle θ is at the optimum incident angle $\theta_{opt}$, the excited SPR photons are smaller and the full-width at half maximum of the electric field strength E is larger, so that the enhancement of the electric field strength E is much smaller than about 90 times of incident light.

Next, at step 903, an optimum thickness $t_3$ of the $SiO_2$ protection layer 3 is selected. FIG. 13 was obtained by a simulation using the above-mentioned simulation software WinSpall (trademark) which calculates a reflectivity R of light reflected form the incident/reflective surface $F_1$ of the Ag layer 2' where the thickness $t_2'$ of the Ag layer 2' is fixed at 42 nm while the thickness $t_3$ of the $SiO_2$ protection layer 3 is changed from 0 to 200 nm. In order to simplify the description, only six ATR signal spectrums at $t_3$=0 nm, 10 nm, 40 nm, 80 nm, 160 nm and 200 nm are illustrated in FIG. 13.

In FIG. 13, the simulation conditions under the wavelength λ=880 nm of the infrared laser ray IR1 are as follows:
(1) For the BK-7 prism 1,
the refractive index $n_1$ is 1.535: and
the extinction coefficient $k_1$ is 0.
(2) For the Ag layer 2',
the thickness $t_2'$ is 42 nm;
the refractive index $n_2'$ is 0.163: and
the extinction coefficient $k_2'$ is 6.
(3) For the $SiO_2$ protection layer 3,
the thickness $t_3$ is variable;
the refractive index $n_3$ is 1.5: and
the extinction coefficient $k_3$ is 0.

As shown in FIG. 13, since the $SiO_2$ protection layer 3 has no absorption loss ($k_3$=0), when the thickness $t_3$ of the $SiO_2$ protection layer 3 is increased, the plasmon dip angle is shifted toward a higher angle where the depth of the plasmon dip is at a point of R=0, so that SPR photons can be excited regardless of the thickness $t_3$ of the SiO protection layer 3. In this case, the narrower the full-width at half maximum of the plasmon dip, the larger the electric field strength E. Therefore, in order to increase the strength of the scattered light SL from the fine particles P, the $SiO_2$ protection layer 3 would be unnecessary. However, in the same way as in the first embodiment, the thickness $t_3$ of the $SiO_2$ protection layer 3 is selected to prevent the Ag layer 2' from being flawed.

Figure 15:
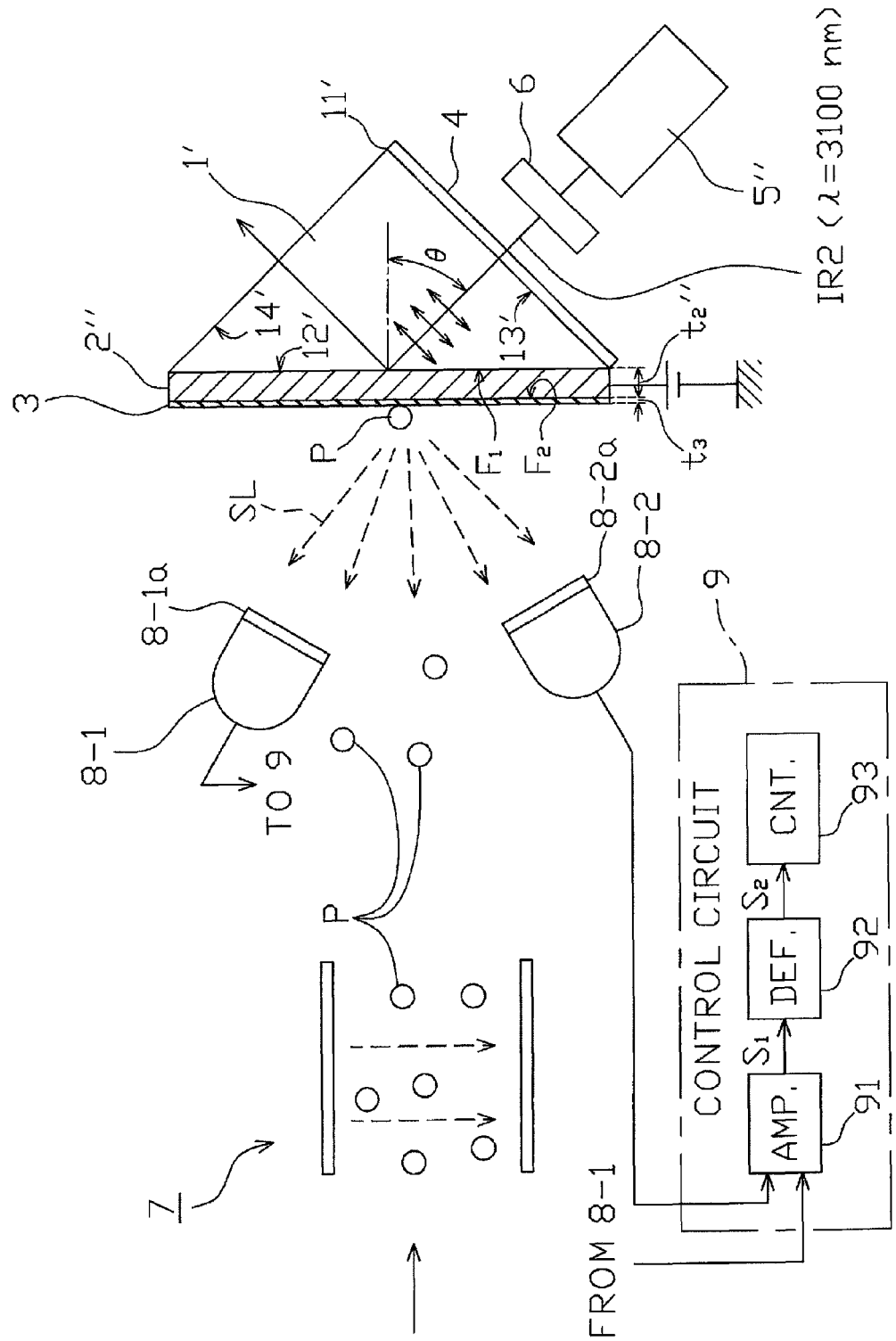
FIG. 15 is a partly cross-sectional view illustrating a third embodiment of the particle detector according to the presently disclosed subject matter.

In FIG. 15, which illustrates a third embodiment of the particle detector according to the presently disclosed subject matter, a sapphire prism 1' is provided instead of the BK-7 prism 1. Also, a platinum (PT) layer 2" as a metal layer is deposited by an evaporating process or a sputtering process on a surface 12' of the sapphire prism 1', instead of the Au layer 2 of FIG. 1, and a infrared laser source 5" for emitting an infrared laser relay IR2 whose wavelength λ is 3100 nm, instead of the He—Ne laser source 5 of FIG. 1.

The sapphire prism 1' as a transparent body has a refractive index $n_1'$ of 1.71 and a vertical angle of 90°.

In the same way as the Au layer 2 of FIG. 1, the Pt layer 2" is about 1 cm long, and its thickness $t_2"$ is selected within about 10 nm to 10 μm. Also, an about 1 to 2 nm thick metal layer made of Cr or the like may be deposited on the surface of the sapphire prism 1' to enhance the contact characteristics between the Pt layer 2" and the sapphire prism 1'.

In the same way as in FIG. 1, an anti-reflection (AR) coating layer 4 is coated on a surface 13' of the sapphire prism 1'. In this case, an arris 11' of the sapphire prism 1' is formed by the surface 13' as well as a surface 14'. Note that, if the incident loss by the reflectivity such as 8% of the sapphire prism 1' is negligible, the AR coating layer 1 can be omitted.

Note that, SPR photons are generated by irradiating the Pt layer 2" with the infrared laser ray IR2 of the infrared laser source 5"; however, since the wavelength of light capable of exciting SPR photons by the Pt layer 2" is ranged from about 3000 nm to 12000 nm, other light sources than the infrared laser source 5" can be used. In this case, a wavelength of an infrared light region close to the SPR wavelength 300 nm of Pt is preferable to detect fine particles P in view of the wavelength reducing effect.

Also, instead of the high directivity and high coherent laser light, inexpensive monochromatic light source such as light emitting diodes (LEDs) can be used to emit monochromatic light which would exhibit almost the same effect as the laser light by a suitable optical design in consideration of the directivity and deflection characteristics.

The operational principle of the particle detector of FIG. 15 is the same as that of the particle detector of FIG. 1 which uses the electric field enhancing effect and the wavelength reducing effect of SPR photons.

Figure 16:
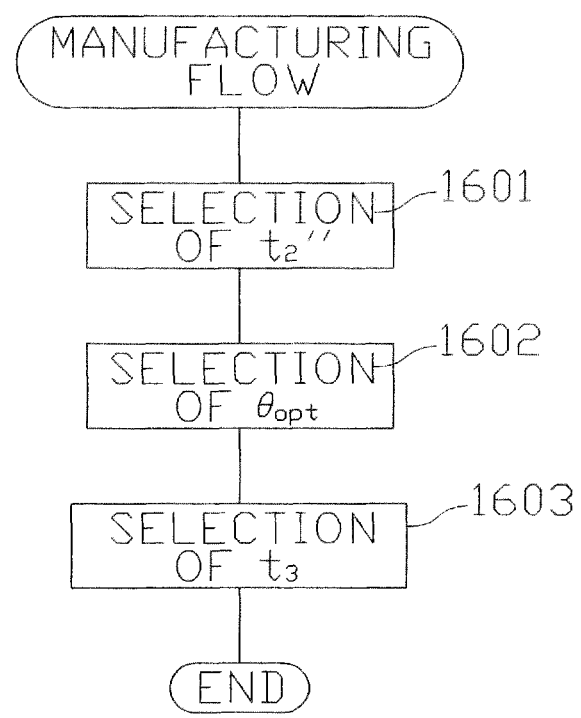
FIG. 16 is a flowchart for illustrating a manufacturing flow of the particle detector of FIG. 15.

FIG. 16 is a flowchart for explaining a manufacturing flow of the particle detector of FIG. 15.

First, at step 1601, an optimum thickness $t_2''$ of the Pt layer 2" is selected. That is, if the incident angle θ of the infrared laser ray IR2 at the incident/reflective surface $F_1$ of the Pt layer 2" is an optimum incident angle $\theta_{opt}$ (>$\theta_c$ where $\theta_c$ is a critical angle), the number of SPR photons excited on the photoelectric surface $F_2$ of the Pt layer 2" of FIG. 15 is maximum. In other words, when $\theta=\theta_{opt}>\theta_c$, the reflectivity R at the incident/reflective surface $F_1$ of the Pt layer 2" is minimum. In this case, FIG. 17 was obtained by a simulation which calculates a reflectivity R of light reflected form the incident/reflective surface $F_1$ of the Pt layer 2" by angularly scanning the sapphire prism 1' with the infrared laser ray IR2. This simulation can be carried out by the simulation software WinSpall (trademark) developed by Max Planck Institute.

Figure 17:
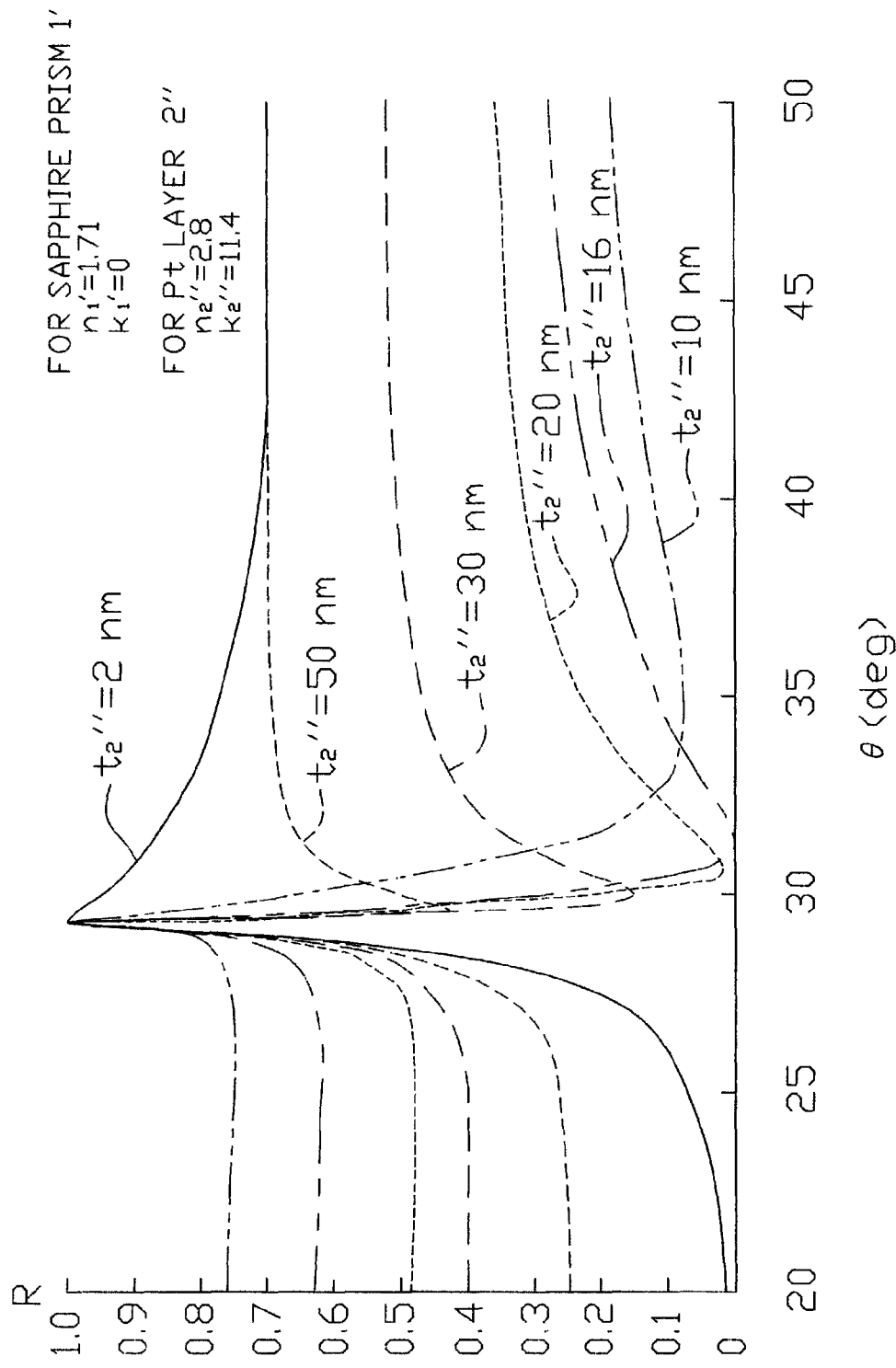
FIG. 17 is an ATR signal spectrum diagram for explaining selection of the thickness $t_2''$ of the Pt layer at step 1601 of FIG. 16.

FIG. 17, the simulation conditions under the wavelength λ=3100 nm of the infrared laser ray IR2 are as follows:
(1) For the sapphire prism 1',
the refractive index $n_1'$ is 1.71: and
the extinction coefficient $k_1'$ is 0.
2) For the Pt layer 2",
the refractive index $n_2''$ is 2.8;
the extinction coefficient $k_2''$ is 11.4: and
the thickness $t_2''$ is variable.
(3) For the SiO₂ protection layer 3,
the thickness $t_3$ is 0.
That is, the SiO₂ protection layer 3 is assumed to be absent.

FIG. 17, only one ATR signal spectrum of the Pt layer 2" whose thickness $t_2''$ is 16 nm is selected from a plurality of ATR signal spectrums of the Pt layer 2" whose thickness $t_2''$ is variable, i. e., 2 nm, 10 nm, 16 nm, 20 nm, 30 nm and 50 nm. That is, the ATR signal spectrum of FIG. 17 shows that, if the thickness $t_2''$ of the Pt layer 2" is smaller than 10 nm, the Pt layer 2" cannot sufficiently absorb evanescent photons generated therein, and if the thickness $t_2''$ of the Pt layer 2" is larger than 50 nm, the generation of evanescent photons in the Pt layer 2" is attenuated, so as not to excite SPR photons in the Pt layer 2", thus increasing the reflectivity at a plasmon dip. Although not illustrated in FIG. 17, from FIG. 18A, the ATR signal spectrum at $t_2''$=16 nm shows a sharp plasmon dip where the reflectivity R is 0. Therefore, the thickness $t_2''$ of the Pt layer 2" is selected to be 16 ±1 nm, so that the excited SPR photons are maximum.

Figure 18A:
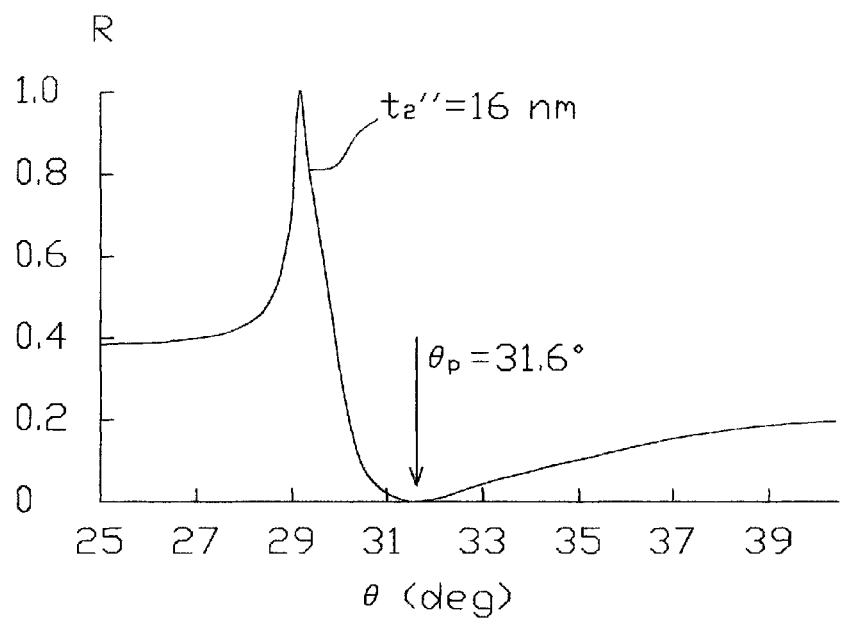
FIGS. 18A and 18B are an ATR signal spectrum diagram and an electric field strength diagram, respectively, for explaining selection of the optimum incident angle $\theta_{opt}$ at step 1602 of FIG. 16.
Figure 18B:
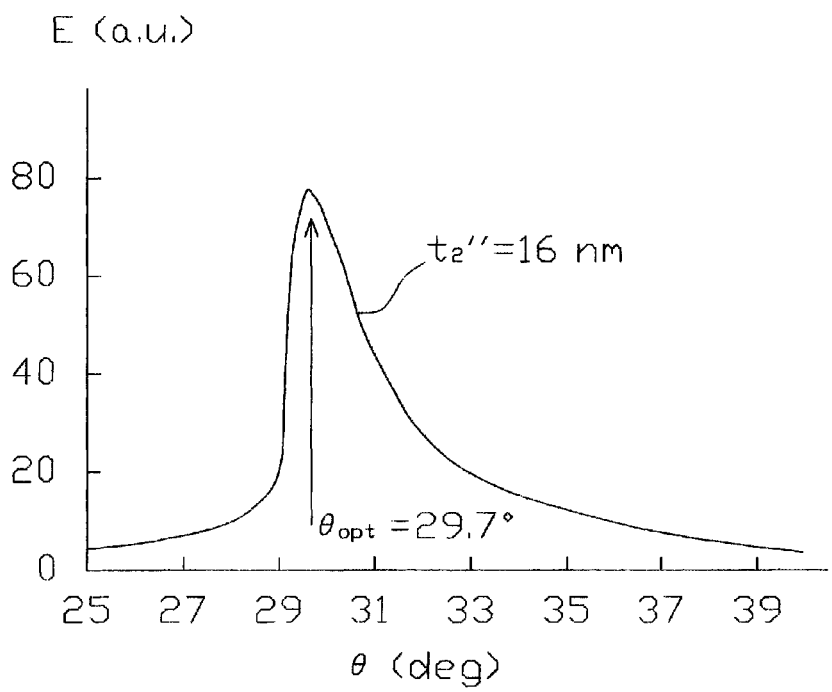
Figure 19A:
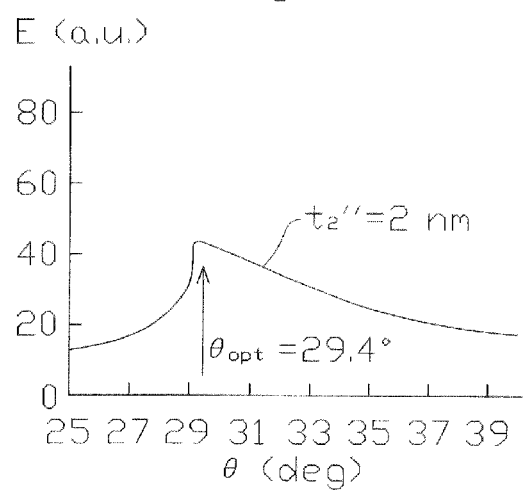
FIGS. 19A, 19B, 19C and 19D are electric field strength diagrams for explaining the optimum incident angle $\theta_{opt}$ of FIGS. 18A and 18B.
Figure 19B:
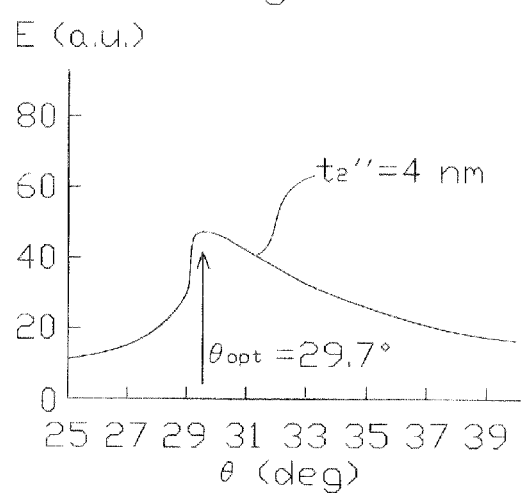
Figure 19C:
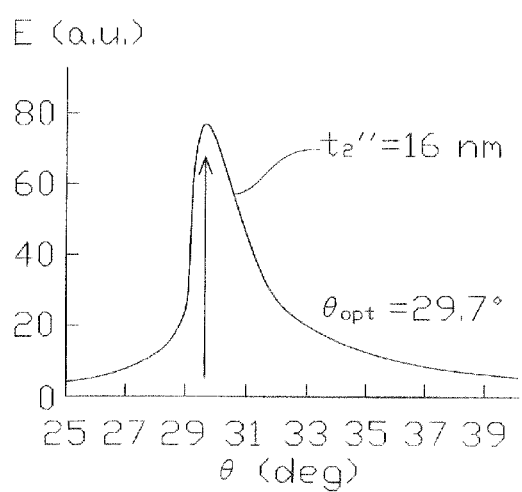
Figure 19D:
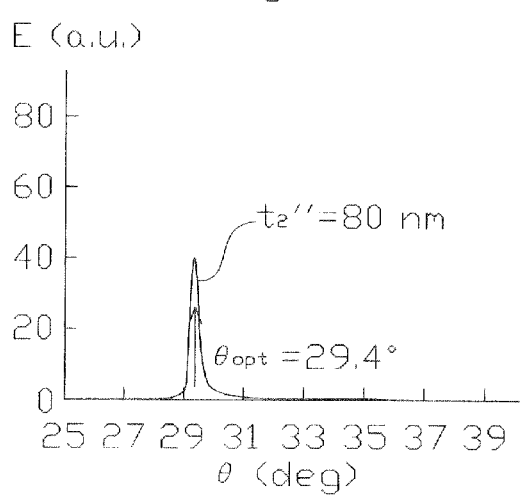

Next, at step 1602, an optimum incident angle $\theta_{opt}$ is selected. As illustrated in FIG. 18A, when the incident angle θ is a plasmon dip angle $\theta_p$ (=31.6°), the excited SPR photons are maximum. However, as illustrated in FIG. 18B, the electric field strength E is maximum when the incident angle θ=29.7° which is a little smaller than the plasmon dip angle $\theta_p$ (=31.6°). Therefore, in order to exhibit the electric field strength enhancing effect by the SPR photons, the optimum incident angle $\theta_{opt}$ is selected at 29.7°. In this case, the electric field strength E is enhanced by about 90 times that of the incident light. This larger enhancement of the electric field strength of the third embodiment than that of the first embodiment is due to the difference in extinction coefficient between the Pt layer 2" and the Au layer 2.

As illustrated in FIGS. 19, 19B, 19C and 19D, when the thickness $t_2''$ of the Pt layer 2" is 2 nm or 4 nm smaller than 16 nm, or 80 nm larger 16 nm even if the incident angle θ is at the optimum incident angle $\theta_{opt}$, the excited SPR photons are smaller and the full-width at half maximum of the electric field strength E is larger, so that the enhancement of the electric field strength E is much smaller than about 8 times of incident light.

Figure 20:
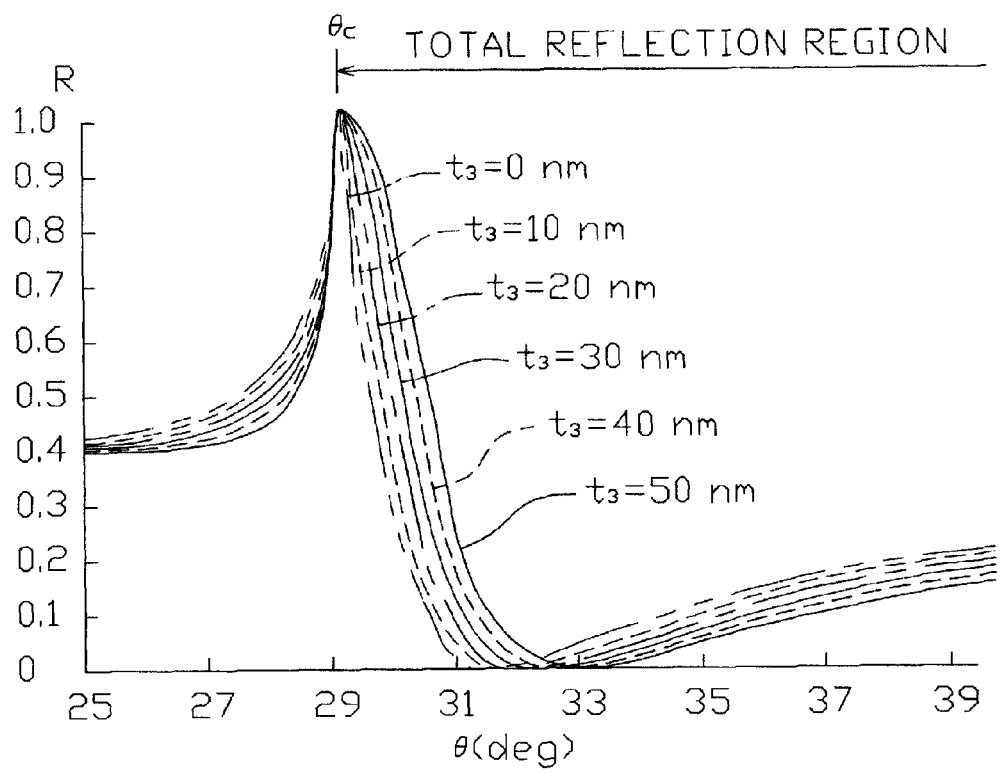
FIG. 20 is an ATR signal spectrum diagram for explaining selection of the thickness $t_3$ of the SiO$_2$ protection layer at step 1603 of FIG. 16.

Next, at step 1603, an optimum thickness $t_3$ of the SiO₂ protection layer 3 is selected. FIG. 20 was obtained by a simulation using the above-mentioned simulation software WinSpall (trademark) which calculates a reflectivity R of light reflected form the incident/reflective surface $F_1$ of the Pt layer 2" where the thickness $t_2''$ of the Pt layer 2" is fixed at 16 nm while the thickness $t_2$ of the SiO₂ protection layer 3 is changed from 0 to 50 nm. In order to simplify the description, only six ATR signal spectrums at $t_3$=0 nm, 10 nm, 20 nm, 40 nm and 50 nm are illustrated in FIG. 20.

In FIG. 20, the simulation conditions under the wavelength λ=3100 nm of the infrared laser ray IR2 are as follows:
(1) For the sapphire prism 1',
the refractive index $n_1'$ is 1.71: and
the extinction coefficient $k_1'$ is 0.
(2) For the Pt layer 2",
the thickness $t_2''$ is 16 nm;
the refractive index $n_2''$ is 2.8: and
the extinction coefficient $k_2''$ is 11.4.
(3) For the SiO₂ protection layer 3,
the thickness $t_3$ is variable;
the refractive index $n_3$ is 1.5: and
the extinction coefficient $k_3$ is 0.

As shown in FIG. 20, since the SiO₂ protection layer 3 has no absorption loss ($k_3$=0), when the thickness $t_3$ of the SiO₂ protection layer 3 is increased, the plasmon dip angle is shifted toward a higher angle where the depth of the plasmon dip is at a point of R=0, so that SPR photons can be excited regardless of the thickness $t_3$ of the SiO₂ protection layer 3. In this case, the narrower the full-width at half maximum of the plasmon dip, the larger the electric field strength E. Therefore, in order to increase the strength of the scattered light SL from the fine particles P, the SiO₂ protection layer 3 would be unnecessary. However, in the same way as in the first embodiment, the thickness $t_3$ of the SiO₂ protection layer 3 is selected to prevent the Pt layer 2" from being flawed.

Figure 21:
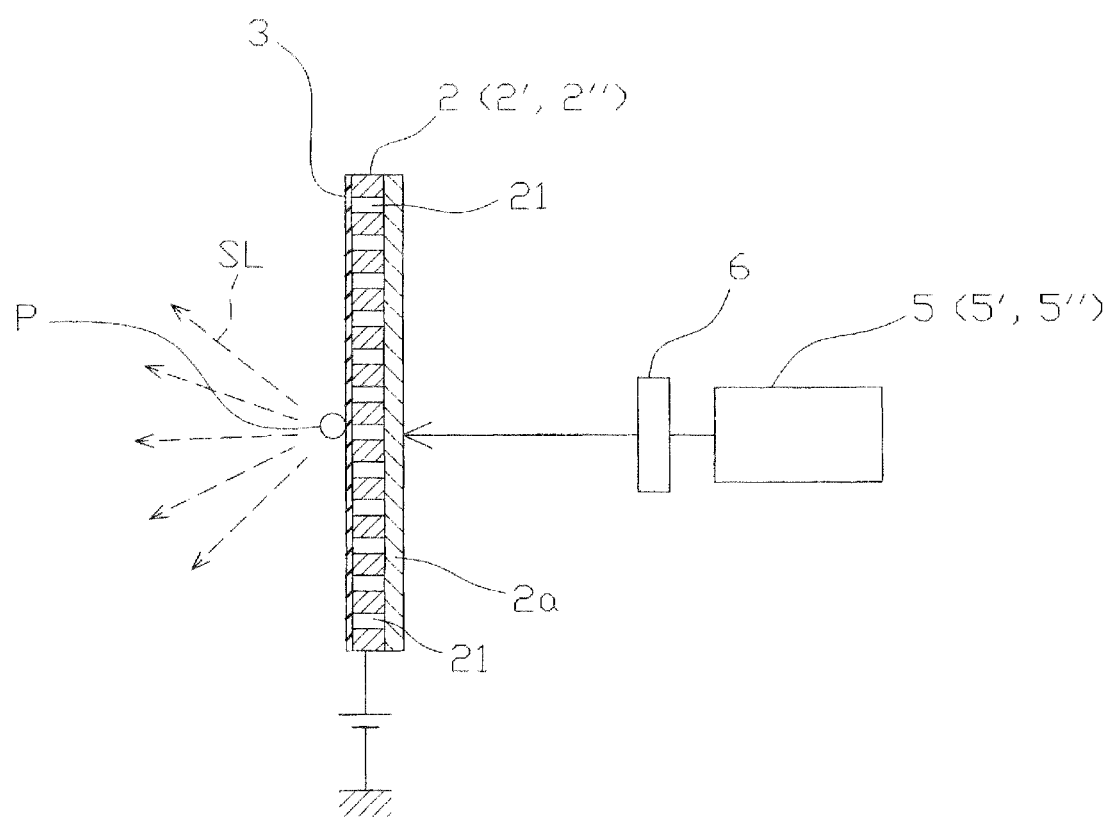
FIG. 21 is a cross-sectional view illustrating a modification of the particle detector of FIG. 1, 8 or 15.

FIG. 21 is a cross-sectional view illustrating a modification of the particle detector of FIG. 1, 8 or 15, and FIG. 22 is a plan view of the modification of FIG. 21.

Figure 22:
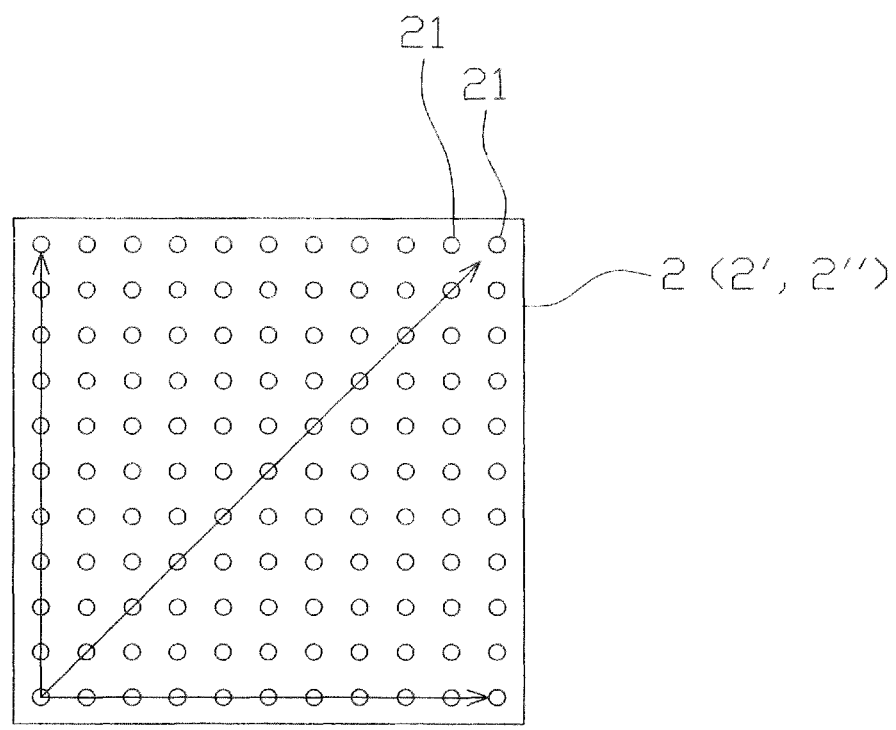
FIG. 22 is a plan view of the metal layer of FIG. 21.

As illustrated in FIGS. 21 and 22, holes 21 are regularly perforated in the Au layer 2, the Ag layer 2' or the Pt layer 2". In this case, the hoes 21 have a diameter smaller than the wavelength λ of the visible laser ray V, the infrared laser ray IR1 or IR2. Therefore, when the visible laser ray V, the infrared laser ray IR1 or IR2 is incident to the incident/reflective surface $F_1$ of the Au layer 2, the Ag layer 2' or the Pt layer 2", a part of the visible laser ray V, the infrared laser ray IR1 or IR2 is incident into the holes 21, so that this part is hardly radiated form the holes 21 due to the small diameter thereof, while evanescent photons are generated in the Au layer 2, the Ag layer 2' or the Pt layer 2". This phenomenon is known as means for generating evanescent photons using very small holes. Additionally, as indicated by arrows in FIG. 22, evanescent photons generated in one of the holes 21 propagate into an adjacent one of the holes 21 to enhance the intensity of the evanescent photons. As a result, SPR photons are easily excited on the photoelectric surface $F_2$ of the Au layer 2, the Ag layer 2' or the Pt layer 2" by the enhanced evanescent photons.

In FIG. 21, in order to simplify the description, the ionizer 7, the photomultipliers 8-1 and 8-2, and the control circuit 9 of FIGS. 1, 8 and 15 are omitted.

Also, in FIG. 21, a surface plasmon (SP) abnormal penetration phenomenon would occur to enhance so-called background light at a specified wavelength and angle which is incident to the detector (i. e., the photomultipliers 8-1 and 8-2 of FIGS. 1, 8 and 15). As a result, the scattered light SL from the fine particles P may be buried in the background light. In view of this, it should be avoided to use the above-mentioned specified frequency inviting the SR abnormal penetration phenomenon to excite the SPR photons.

Note that, since the above-mentioned the SR abnormal penetration phenomenon is due to the interference effect by the regular arrangement of the holes 21, the SR abnormal penetration phenomenon can be avoided by giving a little disorder to the regular arrangement of the hoes 21.

Also, the particle detector of FIG. 21 is manufactured in accordance with the manufacturing flow of FIG. 2, 9 or 16 except for the selection of the optimum incident angle $\theta_{opt}$ at step 202, 902 or 1602.

Figure 23:
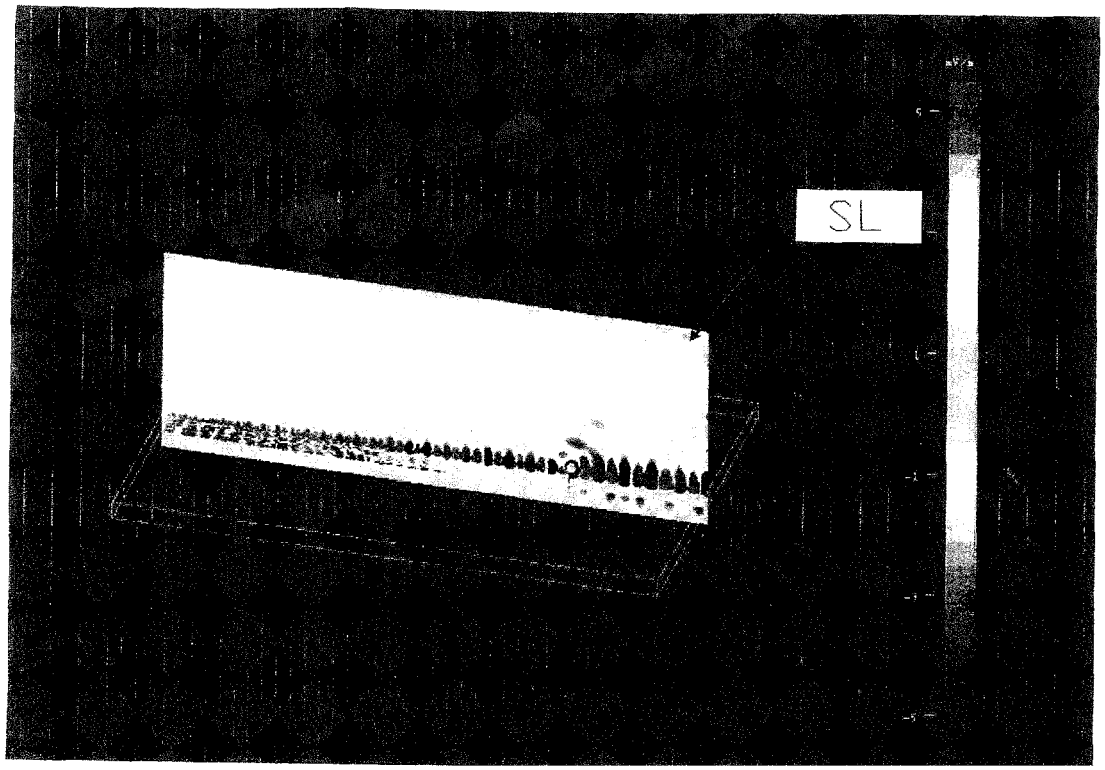
FIG. 23 is a photograph showing a simulation result of surface plasmon resonance (SPR) photons of the particle detector of FIG. 8.
Figure 25:
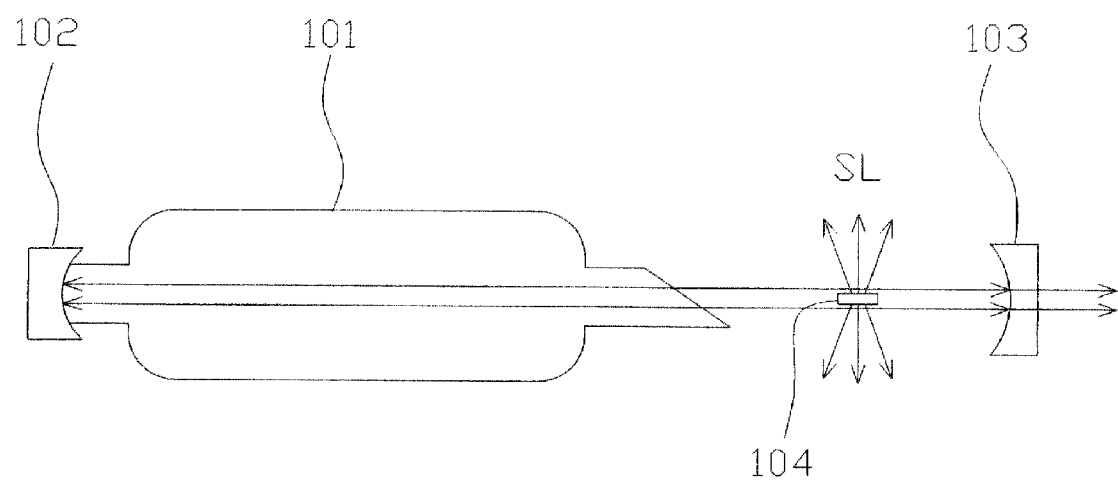
FIG. 25 is a diagram illustrating a first prior art particle detector.
Figure 26:
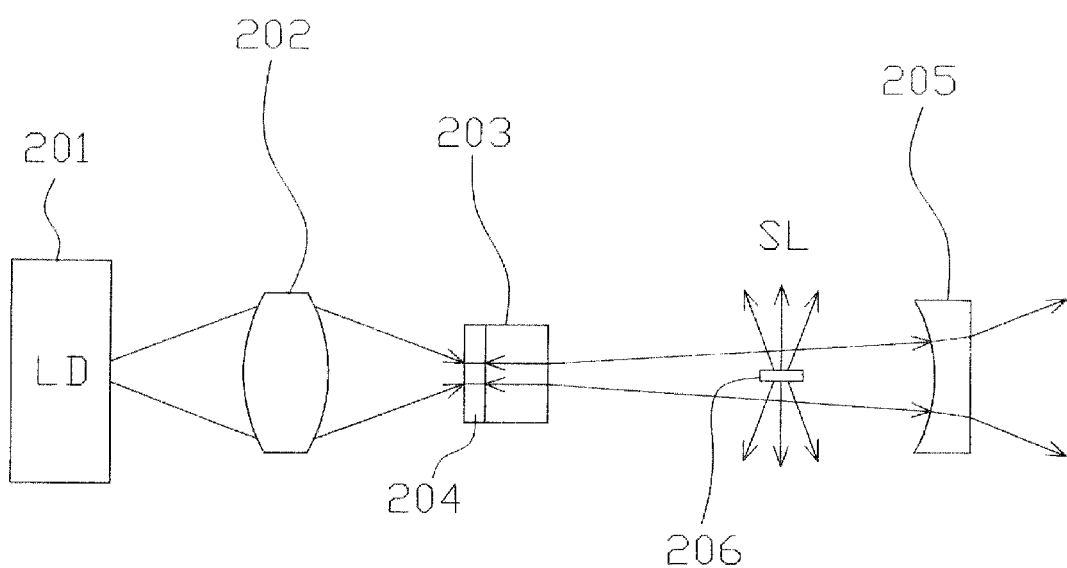
FIG. 26 is a diagram illustrating a second prior art particle detector.

In FIG. 23, which is a photograph showing a simulation result of scattered light by SPR photons using a finite difference time domain method, near-field SPR photons excited on the surface of the Ag layer 2' have a large amplitude 5 mV/m of electric field. Therefore, when a fine particle having a diameter of 0.1 μm is deposited to the surface of the Ag layer 2', large far-field scattered light with a large amplitude 0.3 μV/m of electric field is generated at a location which is about 1 cm distant from this fine particle. In this case, the strength of the scattered light is represented by the incident light strength·$[0.3~\mu V/m \cdot 3~mVm]^3$.

Therefore, if the strength of incident light is 100 mW, the strength of scattered light is 1 nW which can be sufficiently detected by the photomultipliers 8-1 and 8-2 of FIG. 8 with a high sensitivity.

Also, in the above-described embodiments, when the metal layer such as the Au layer 2, the Ag layer 2' and the Pt layer 2" is grown by an evaporating process or a sputtering process on the BK-7 prism 1 or the sapphire prism 1', grains of the metal layer are grown. The size "g" of the grains of the metal layer affects the detection sensitivity of the scattered light SL of the fine particles P. That is, when the size "g" of the grains of the metal layer is large, the scattering of the near-field SPR photons excited on the surface of the metal layer is so large that the near-field SPR photons are buried in background light to reduce the sensitivity of the scattered light SL of the fine particles P. In this case, the strength of the background light caused by near-field SPR photons excited on the surface of the metal layer is proportional to $g^6$ (see: the formula (1). On the other hand, since the grains of metal of the metal layer are arranged on the surface thereof, the strength of the above mentioned background light per unit area is inversely proportional to $g^2$. As a result, the strength of the background light caused by the near-field SPR photons excited on the surface of the metal layer per unit area is proportional to $g^4$ ($=g^6/g^2$).

FIG. 24 is a table showing a relationship between the size "g" of grains and relative background light strength of metals. As illustrated in FIG. 24, the size "g" of grains of Au is about 60 nm. Note that the size "g" of grains of Au is almost the same regardless of whether Au is grown by an evaporating process or by a sputtering process. In addition, the size "g" of grains of Ag is almost the same as that of Au. On the other hand, the size "g" of grains of Pt is about 12 nm when Pt is grown by a sputtering process. Note that the size "g" of grains of Pt grown by an evaporating process is a little larger then 12 nm. Therefore, if the size "g" of grains of the Pt layer 2" of the third embodiment is 1, the size "g" of grains of the Au layer 2 of the first embodiment and the Ag layer 2' of the second embodiment "g" is $(60/12)^4 \approx 600$. Thus, the strength of the background light of the third embodiment using the Pt layer 2" is remarkably smaller than those of the first and second embodiments using the Au layer 2 and the Ag layer 2', respectively.

In the above-described embodiments, other prisms made of CaF, BaF, LiF or MgF can be used instead of the BK-7 prism 1 or the sapphire prism 1'. Also, other prisms made of material with a refractive index of less than 2.2 which is no absorption against excited light can be used.

Also, in the above described embodiments, metal layers made of alloys of two or three of Au, Ag and Pt can be used instead of the Au layer 2, the Ag layer 2' and the Pt layer 2". Additionally, any other metal—including materials having a permittivity with a negative imaginary part can be used for such metal layers.

The invention claimed is:

1. A particle detector comprising:
   a light source;
   a metal layer having an incident/reflective surface and a photoelectric surface opposing said incident/reflective surface, wherein incident light from said light source reaches said incident/reflective surface to excite near-field surface plasmon resonance photons at said photoelectric surface, and wherein said near-field surface plasmon resonance photons are changed to far-field scattered light when a particle is deposited on said photoelectric surface of said metal layer; and
   a scattered light detecting unit, provided above said photoelectric surface of said metal layer, for detecting said far-field scattered light.

2. The particle detector as set forth in claim 1, further comprising a particle depositing unit for depositing said particle on said photoelectric surface of said metal layer.

3. The particle detector as set forth in claim 2, wherein said particle depositing unit comprises:
   a particle charging unit for charging said particle; and
   a voltage applying unit for applying a voltage to said metal layer, said voltage having a polarity sign opposite to a polarity sign of said charge particle.

4. The particle detector as set forth in claim 1, further comprising a dielectric protection layer provided on said photoelectric surface of said metal layer.

5. The particle detector as set forth in claim 1, wherein a thickness of said metal layer is selected so that said near-field surface plasmon resonance photons are maximum.

6. The particle detector as set forth in claim 1, wherein an incident angle of said incident light to said metal layer is smaller than a light absorption dip angle by which a reflectivity of said incident light at said incident/reflective surface of said metal layer is minimum in a total reflection region, and is an angle by which strength of an electric field of said incident light at said photoelectric surface of said metal layer is maximum.

7. The particle detector as set forth in claim 1, further comprising a transparent body, formed on said incident/reflective surface of said metal layer, for receiving said incident light from said light source and transmitting said incident light to said metal layer.

8. The particle detector as set forth in claim 7, wherein said transparent body comprises a prism.

9. The particle detector as set forth in claim 8, wherein a surface of said prism on which said metal layer is formed opposed an arris of said prism.

10. The particle detector as set forth in claim 1, wherein said metal layer comprises a gold layer.

11. The particle detector as set forth in claim 1, wherein said metal layer comprises a platinum layer.

12. The particle detector as set forth in claim 1, wherein said metal layer comprises a platinum layer.

13. The particle detector as set forth in claim 1, wherein said metal layer comprises an alloy layer made of at least two of gold, silver and platinum.

14. The particle detector as set forth in claim 4, wherein said dielectric protection layer comprises silicon dioxide.

15. The particle detector as set forth in claim 1, wherein a plurality of holes are perforated in said metal layer, a diameter of each of said holes being smaller than a wavelength of said incident light.

16. The particle detector as set forth in claim 15, wherein said holes are regularly arranged in said metal layer.

17. The particle detector as set forth in claim 16, wherein said scattered light detecting unit comprises an interference filter.

18. The particle detector as set forth in claim 1, wherein said scattered light detecting unit comprises at least one optical waveguide.

* * * * *